(12) United States Patent
Holtlund et al.

(10) Patent No.: US 7,632,462 B2
(45) Date of Patent: Dec. 15, 2009

(54) ASSAY SYSTEM

(75) Inventors: Jostein Holtlund, Oslo (NO); Stig Morten Borch, Oslo (NO); Thorstein Seim, Oslo (NO); Tore Janson, Oslo (NO); Hege Tøn, Oslo (NO); Jan Roger Karlson, Oslo (NO); Inger Lise Lauvstad, Oslo (NO)

(73) Assignee: Axis-Shield ASA, Olso (NO)

( * ) Notice: Subject to any disclaimer, the term of this patent is extended or adjusted under 35 U.S.C. 154(b) by 1028 days.

(21) Appl. No.: 10/476,185

(22) PCT Filed: May 9, 2002

(86) PCT No.: PCT/GB02/02161

§ 371 (c)(1), (2), (4) Date: Apr. 9, 2004

(87) PCT Pub. No.: WO02/090995

PCT Pub. Date: Nov. 14, 2002

(65) Prior Publication Data

US 2004/0161368 A1  Aug. 19, 2004

(30) Foreign Application Priority Data

May 9, 2001 (GB) .................. 0111360.4
Dec. 19, 2001 (GB) .................. 0130359.3

(51) Int. Cl.
*G01N 21/00* (2006.01)
(52) U.S. Cl. ............................ 422/65; 422/66; 422/67; 422/99; 422/100; 436/180; 222/187
(58) Field of Classification Search ........... 422/99–101, 422/65–67; 222/187; 436/180
See application file for complete search history.

(56) References Cited

U.S. PATENT DOCUMENTS

| 5,138,868 A |   | 8/1992 | Long |
| 5,496,523 A |   | 3/1996 | Gazit et al. |
| 5,731,212 A |   | 3/1998 | Gavin |
| 5,833,927 A | * | 11/1998 | Raybuck et al. ............. 422/101 |
| 6,045,757 A |   | 4/2000 | Moriarty et al. |
| 6,117,394 A |   | 9/2000 | Smith |
| 6,194,160 B1 |   | 2/2001 | Levin |

FOREIGN PATENT DOCUMENTS

| JP | 6-58854 | 3/1994 |
| JP | 6-315603 | 11/1994 |
| JP | 8-211071 | 8/1996 |
| JP | 10-62433 | 3/1998 |
| JP | 11-501732 | 2/1999 |
| JP | 11-337557 | 12/1999 |
| WO | WO 97/05492 | 2/1997 |

* cited by examiner

*Primary Examiner*—Jill Warden
*Assistant Examiner*—Jyoti Nagpaul
(74) *Attorney, Agent, or Firm*—Bacon & Thomas, PLLC

(57) ABSTRACT

An assay apparatus comprising: i) an assay cartridge (52,53) comprising at least one well (57-62) and a pipette (50) positionable in at least one said well; ii) a holder arranged to receive said cartridge; iii) drive means operable to position said pipette in selected wells of said cartridge; iv) a gas pressure applicator couplable to said pipette whereby to cause liquid flow through said membrane; and v) a radiation detector operable to detect radiation from a well of said cartridge or from said pipette.

20 Claims, 17 Drawing Sheets

ASSAY SYSTEM

This invention relates to improvements in and relating to assay systems, especially diagnostic assay systems, in particular systems usable at the point-of-care, e.g. at the physician's place of work or at the patient's bedside.

Many diagnostic assays are currently available, e.g. assays for pregnancy, blood sugar, homocysteine, carbohydrate-deficient transferrin, blood-clotting, blood cholesterol, etc. Some such assays are performable by the patient, and some by the patient's physician, but many, especially those which provide a quantitative result, must currently be performed in a laboratory remote from both patient and physician and so result in significant delays between sampling and testing and generally require the patient to make a further visit to the physician to learn the assay's results. This is not only inconvenient to the patient but also increases the costs to the patient or the organization paying for the patient's health care.

There is thus an ongoing need for assay systems, especially ones providing quantitative results, operable by the physician or the physician's colleagues at the point of patient care.

Quantitative assay systems often require highly accurate volume measuring devices, several reagents, and assay-specific result-reading detectors, and it is impractical to provide dedicated assay apparatus for a wide range of different assay systems at the point of care, both for reasons of space and expense.

We have therefore developed an assay apparatus which, in preferred embodiments, is capable of use at the point of care, is capable of performing a range of different assays, is capable of yielding quantitative assay results, and is relatively inexpensive.

Viewed from one aspect the invention provides an assay apparatus, preferably a diagnostic assay apparatus, comprising:

i) an assay cartridge comprising at least two wells and a pipette positionable in at least two of said wells, said pipette having a proximal end and a distal end, said distal end being closed by a liquid permeable membrane;

ii) a holder arranged to receive said cartridge;

iii) drive means operable to position said pipette in selected wells of said cartridge;

iv) a gas pressure applicator couplable to said pipette whereby to cause liquid flow through said membrane;

v) a radiation detector operable to detect radiation from a well of said cartridge or from said pipette; and, optionally but preferably, vi) an electromagnetic radiation source.

Viewed from a further aspect the invention provides an assay cartridge comprising at least two wells and a pipette positionable in at least two of said wells, said pipette having a proximal end and a distal end, said distal end being closed by a liquid permeable membrane.

A pipette is a tube with an aperture at one end (the distal end) into which a liquid may flow on application of a reduced pressure to the other end (the proximal end). In the apparatus referred to in the preceding paragraphs the distal end of the pipette is tipped with (closed by) a liquid permeable membrane. The proximal end of this pipette may be open or closed but if closed then clearly this must be by some means which allows the pressure application necessary for the pipette to function as a pipette. In one embodiment described below, the proximal end of the membrane-tipped pipette is sealed with a pierceable self-sealing membrane (e.g. a rubber gasket) and pressure may be applied through a hollow needle inserted through the membrane. Alternatively the proximal end may be closed by a removeable cap or stopper which is removed to allow pressure application, or by a frangible seal which is broken to allow pressure application.

Viewed from a still further aspect the invention provides an assay device comprising a) a cartridge holder capable of receiving an assay cartridge according to the invention; b) drive means operable to position the pipette of a said cartridge in selected wells of said cartridge; c) a gas pressure applicator couplable to the pipette of a said cartridge whereby to cause liquid flow therethrough; d) a radiation detector operable to detect radiation from a well of a said cartridge or from the pipette thereof; and, optionally but preferably, e) an electromagnetic radiation source.

Thus the combination of the device and the cartridge of the invention provides an assay apparatus according to the invention.

The assay cartridge preferably is provided to the user pre-filled with the reagents required for the particular assay or assays to be performed using that cartridge. Where two or more reagents are required and these should not be mixed before the assay is performed, these may be pre-filled into different wells in the cartridge. Generally such reagents will be prefilled into the wells in measured quantities. Such reagents may for example be liquids, powders, beads, coatings on the well walls, coatings on beads, or materials impregnated into or immobilized on the membrane of the pipette. Where the reagents are liquid or where they are susceptible to degradation on exposure to air or moisture, the cartridge may be sealed to prevent liquid loss or air or moisture access to the susceptible reagent. Such sealing is conveniently achieved by forming the cartridge with a well-containing base and a well-covering cap, and if necessary placing a fluid impermeable seal, e.g. an O-ring, between the well-openings in the base and the well-covering cap, and if desired by placing a removable-seal, e.g. an adhesive sealing strip, about the external junction between cap and base. In another more preferred embodiment, one or more of the wells may be foil sealed before use: in this embodiment the well covering cap is preferably equipped with foil seal cutters for cutting the well-covering foil seals to permit the pipette to be inserted into these wells. Alternatively, the cap may be provided with resilient material at positions corresponding to the tops of the wells (or just the liquid containing wells) such that when cap and base are urged together, a liquid-tight seal is formed at the well tops. Such material may for example be a layer coated onto the cap or discs or gaskets attached (e.g. welded or adhered) to the cap. In one embodiment, the lower surface of the cap is provided with resilient projections capable of functioning as stoppers for the wells. In this way, the stoppers serve to keep cap and base together before use of the cartridge in an assay and after assay performance base and cap can be sealed for disposal simply by urging the two together causing the stoppers again to seal the wells. This is particularly advantageous when the wells following assay performance contain toxic or potentially infectious materials. Such caps can, if desired, be removed before use; however, in a preferred embodiment, the cap will serve to hold the pipette and possibly also to provide attachment means for the pressure applicator. In such an embodiment the drive means may serve to move base relative to cap so as to position the pipette in the desired wells in the different stages of the assay.

In general, and particularly where the cartridge cap is provided with resilient stoppers for the wells in the cartridge base, the apparatus and device of the invention preferably comprise means for separating the cap from the base so that the cartridge may be loaded into the device still sealed. In one embodiment, such separating means comprises a wedge which is moved past the loaded cartridge and engages with projections, e.g. flanges, on cap and base to force the two apart. Desirably this separating means is automatically brought into operation following cartridge loading, e.g. in response to the shutting of the lid to the chamber containing the loaded cartridge or on transport of the cartridge into the chamber for example using a conveyor which can similarly remove the cartridge from the chamber following assay performance.

For different assays, e.g. for different analytes, different assay cartridges may be provided; however, cartridges may be designed for performance of two or more different assays. In this latter case, it will frequently be desirable for the cartridge to contain two or more membrane-capped pipettes, i.e. so that a different pipette can be used for each of the assays.

The wells in the cartridge may be provided in any desired pattern, e.g. as a two dimensional array (e.g. as in conventional multi-well plates), as a linear array, or as a circular array. The use of circular and especially linear arrays is particularly preferred as the mechanism required for moving the cartridge between preset positions is simplified, i.e. the drive means may then operate to move the cartridge along a linear path or to rotate the cartridge.

The use of a linear array of wells is especially preferred, particularly an array comprising, in sequence: a material handling well (optionally before use storing a capillary-tipped pipette removably mounted on the cartridge cap or adapted to receive during use a capillary-tipped pipette mountable on the cartridge cap); a well which before use stores the membrane-tipped pipette or a further capillary tipped pipette mounted on the cartridge cap; and one or a series of two or more (e.g. up to six) wells for assay performance and assay result reading—these wells may contain reagents and before use such reagent containing wells may be foil sealed and one of these wells may be open ended or open-sided to facilitate result reading. In such an arrangement, the cap and base may desirably be separated before assay performance begins and re-engaged only when assay performance is completed. Thus result reading in this arrangement takes place while cap and base are disengaged from each other. In this arrangement, the cap and base are preferably latched together, e.g. by a snap-lock latch. The material handling well may for example contain dry reagent for mixing during assay performance, a filter for sample separation (e.g. to remove erythrocytes from a blood sample), or a further pipette capable of mating engagement with a cap-mounted pipette (e.g. a capillary-tipped pipette).

While the cartridge must contain at least two wells, one or more positions in the well array of a multi-well cartridge may be open-ended or open-sided such that detection of radiation from the pipette when located in such positions is facilitated. If radiation from a pipette in a well is to be detected, then at least a portion of the well wall must be transparent to the type of radiation to be detected.

The wells in the cartridge may remain stationary during the assay; however, as it may be desirable to use the detector to monitor the progress of the assay, it is generally preferable that the drive means is operable to move the cartridge between two or more pre-set positions so that the detector can detect radiation from different cartridge wells. Alternatively but less preferably, the detector itself may be movable between pre-set positions or movable mirrors may be provided so as to permit the light path from cartridge to detector to be varied to achieve the same effect.

Thus in a preferred embodiment the drive means will operate during the assay to lift the cartridge cap and pipette away from the well-containing base (or more preferably to drop the base away from the cap), to move the base relative to the cap (preferably by moving the base, e.g. linearly or by rotation) to bring the pipette into registry with the desired well, and to move cap and base together to place the pipette into the desired well, and so on until the assay is complete.

In some assays it may be desirable to tilt the wells during liquid transfer or to agitate liquid in a well and accordingly it is desirable that the drive means also be operable to tilt or agitate (e.g. rock or shake) at least the well-containing portion of the cartridge.

The drive means may be manually operable, e.g. a mechanical drive or a motor driven drive activated at each stage by the operator; however it will preferably be a motor drive activated to perform the required actions by an external or more preferably internal computer which operates the assay apparatus.

The wells in the cartridge may be of any desired shape or volume; however preferably they will be straight-sided cylindrical or less preferably tapered cylindrical. The cross-section of such cylindrical wells may be of any desired shape, e.g. circular, oval, polygonal (e.g. rectangular), semicircular, etc. The well bases may be flat or curved; however for wells which are to be monitored from below during or at the end of the assay, the well base will preferably be flat. In a particularly preferred embodiment, the well base is flat and sloping, i.e. non-horizontal. The wells may be within a solid base or alternatively, and less preferably, the wells may be connected in a strip, plate, disc, daisy-wheel, etc. format. The well walls, for example the solid well-containing base, will preferably be of plastic, especially light-transparent plastic, e.g. acrylic, vinylic, styrenic or olefinic plastic. The choice of the particular plastic will however depend, as is conventional, on the nature of the reagents used. It has been found particularly preferable to use plastics with good optical properties and low gas and/or liquid permeability. To this end, copolymers of alpha-olefins (e.g. ethylene and propylene, especially ethylene) and cyclic olefins (e.g. norbornene) are especially preferred, e.g. the product sold under the trade name Topas® 8007 by Ticona GmbH of Frankfurt, Germany (Topas® 8007 is an ethylene/norbornene copolymer). Desirably such copolymers have a light transmission (measured according to ASTM D1003 for a 2 mm wall thickness) of at least 80%, most preferably at least 90%; and a water vapour permeability (at 23° C. and 85% RH, measured according to DIN 53122 on a 80×80×1 mm sample) of less than 0.2 g.mm.m$^{-2}$d$^{-1}$, more preferably less than 0.05 g.mm.m$^{-2}$d$^{-1}$.

Typically, the wells will have internal diameters of 3 to 20 mm, especially 5 to 15 mm, and volumes of 0.1 to 5 mL, especially 0.5 to 1.5 mL.

The membrane-tipped pipette in the cartridge of the invention is preferably cylindrical and the membrane is preferably at or more preferably covering one end. The other, open, end is preferably shaped for substantially gas-tight attachment to a pressure applicator. The pipette may be of any appropriate material; however transparent plastic or glass is preferred. The membrane may be attached to the pipette in any appropriate fashion, e.g. by welding (e.g. ultrasonic or thermal welding), adhesive, fusion of a granular membrane precursor, etc.

The membrane itself may be of any appropriate material, e.g. plastics (e.g. nylon, polysulphones, etc.), glass (e.g. glass fibre), metal, etc. However cellulosic-membranes (e.g. reinforced nitrocellulose) are especially preferred as it is relatively straightforward to immobilize antibodies or other assay reagents on such materials.

In various embodiments of the invention, the membrane is preferably planar and perpendicular to the pipette axis; such membranes are particularly effective for removal of liquid from a horizontal flat- or concave-bottomed well.

The membrane however may alternatively and more preferably be planar but angled relative to the axis of the pipette, e.g. up to 85° off perpendicular to the axis, preferably 10 to 80° off perpendicular, more preferably 50 to 70° off perpendicular, especially about 60° off perpendicular. Where the pipette and one or more of the wells is rectangular (e.g. square) in cross-section, it is preferred that the membrane be angled and that the base of one or more such wells likewise be angled so as to be substantially parallel to the membrane when the pipette is in that well.

The use of a sloping membrane is especially advantageous as for a given pipette cross-sectional area, the surface area of the membrane is increased as it is angled progressively further from the horizontal, so giving a larger surface area to be read or monitored during the assay. Most surprisingly, not only do sloping membranes allow essentially all of the contents of a correspondingly shaped well to be taken up through the membrane but also the uptake is uniform across the membrane (i.e. if a coloured analyte becomes trapped on the membrane the membrane becomes uniformly coloured). A further advantage is that the membrane may be viewed from the side avoiding any risk of droplets of sample, reagent, etc., falling onto the apparatus optics. A still further advantage is that the membrane may readily be illuminated without causing high incidence of the illuminant light being reflected into the light detector. Another advantage is that, even with a coloured sample (e.g. blood), it is possible to monitor the membrane surface through the well side wall and thus to terminate any reaction step when the desired change in membrane surface has occurred as the membrane-to-well wall spacing can be less than that for a horizontal membrane in a liquid-containing well. A yet still further advantage is that the formation of bubbles between the membrane and the facing well wall is reduced relative to the case for horizontal membranes so reducing the need to tilt or shake the cartridge base.

The use of angled membrane tipped pipettes is thought to be novel and thus viewed from a further aspect the invention provides a pipette the distal end whereof is cylindrical and tipped by a porous membrane the outer surface whereof is angled away from the plane perpendicular to the cylindrical axis of said distal end, said pipette preferably forming part of a diagnostic assay cartridge.

The use of a rectangular cross-section for a well is especially preferred as it reduces the incidence of liquid reagents being trapped at the upper end of wells by capillary effects following inversion of the assay cartridges during transport or storage. The corners where well side walls meet should therefore desirably be as sharp as possible at the upper ends of the wells, e.g. having a radius of curvature of 0.5 mm or less, e.g. 0.1 mm or less. However, to prevent liquids in the base of the wells creeping up the corners of the well, it is desirable that at the lower end of the wells the corners should be chamfered or more rounded, e.g. having a radius of curvature of at least 0.5 mm, preferably at least 0.8.mm.

Where a well is to be used for assay reading, e.g. where the absorption of light passing through a liquid in the well is to be measured, it is also particularly preferred to use a rectangular cross-section well with an angled base. In this way, by appropriate masking of the section of the well visible to the detector, one may choose to measure light transmitted through the full width of the well or through a narrower width at the base of the well (i.e. between a side wall and the sloping base). Thus the light path length through the well may be increased or decreased by moving the visible section up or down. In this way, for example, where the optical density of the well-contents is high, a shorter path length may be chosen.

Moreover, by measuring light transmission intensity at two or more path lengths (e.g. within and above the tapered base portion of the well), the contribution of the well walls to the detected signal can be determined and corrected for.

Where scattered light is to be detected (e.g. where the sample being read contains particles or agglomerates or is fluorescent or phosphorescent), it will again be desirable to use rectangular cross-section wells with the incident light being directed perpendicular to one pair of well walls and with the scattered light being detected by a detector (e.g. digital camera) directed at one of the other walls. Where the cartridge contains a linear array of wells, the reading well for light scattering measurements is preferably at one end of the array.

This use of angled wall wells is also novel and forms further aspects of the invention.

Viewed from a further aspect the invention thus provides an assay apparatus comprising:

i) an assay cartridge comprising at least one well and a pipette positionable in at least one said well, at least one said well having two parallel planar side walls joined by a base wall comprising at least one planar face the normal to the surface whereof is coplanar to and non-perpendicular to normals to the parallel planar surfaces of said side walls;

ii) a holder arranged to receive said cartridge;

iii) drive means operable to position said pipette in selected wells of said cartridge;

iv) a gas pressure applicator couplable to said pipette whereby to cause liquid flow through said membrane; and v) a radiation detector operable to detect radiation from a well of said cartridge or from said pipette.

In this aspect the base is preferably planar, angled to the horizontal as described above, and the well is preferably rectangular in cross-section. The cartridge moreover preferably contains at least one capillary-tipped pipette and/or membrane-tipped pipette, again as described herein.

Viewed from a still further aspect the invention provides an assay cartridge comprising at least one well and a pipette positionable in at least one said well, at least one said well having two parallel planar side walls joined by a base wall comprising at least one planar face the normal to the surface whereof is coplanar to and non-perpendicular to normals to the parallel planar surfaces of said side walls.

In addition to a membrane-tipped pipette, the cartridges of the invention may contain one or more further pipettes, again preferably carried by the cartridge cap, for example for measuring out an accurate volume of reagent or sample or for mixing reagents and samples. In one preferred embodiment the cartridge contains a capillary-tipped pipette which draws up a desired amount of fluid from a sample by virtue of its capillary action. Particularly desirably this comprises a capillary opening into a chamber of wider internal diameter such that capillary action causes only the capillary tip to fill. With the tip withdrawn from the surrounding liquid, the contents of the tip can then be ejected into a cartridge-well under pressure or sucked up further into the pipette beyond the capillary tip and chamber.

In another aspect of the invention, the cartridge may comprise a capillary-tipped pipette in place of the membrane-tipped pipette. As will be discussed further below, such a cartridge may for example be used in a clotting time assay.

The external diameter of the membrane-tipped pipette is preferably at least 0.8 mm, e.g. 1 to 5 mm, especially 1.5 to 2.5 mm, less than the internal diameter of the wells so as to facilitate gas flow between well wall and pipette during liquid transfer across the pipette membrane and to ensure substantially complete uptake of liquid from the wells. The gap also allows the well to contain liquid (e.g. 200 μL) and the membrane-tipped pipette before uptake of liquid into the pipette.

While the pipette and the wells may have the same form of cross-sectional shape (i.e. circular, square, etc.), it may occasionally be preferred that the shapes differ slightly, e.g. one being circular and the other elliptical, as this reduces the risk of the membrane-tipped pipette being held by suction to the bottom of a well. This problem may similarly be addressed by making the pipette tip or the well base slightly irregular, e.g. with indentations or projections.

In a particularly preferred embodiment, the cartridge comprises: a base containing a plurality, e.g. 2 to 8 or 10, of wells, at least two and preferably at least 3 of which are free of liquid reagents and at least one of which contains a liquid reagent; and a cap carrying the membrane-tipped pipette such that it is disposed with the membrane end in one of the empty wells and with the open end accessible on the outer surface of the cover, and having a sample application aperture through the cover to communicate with another of the liquid-free wells. Desirably removable seals are provided to cover the open ends of the pipette and the sample application aperture. Unless the cap carries well-sealing stoppers or the wells are sealed as described above, a further removable seal will preferably be provided to surround the external junction of cap and base and O-ring or other seals will be provided around at least the liquid containing wells between cap and base. In either of these ways the interior of the cartridge is isolated from air and moisture before use. The base and cap preferably have indentations or projections for engagement with the cartridge holder and drive means, for ensuring correct registry between cap and base during assay performance, and if the cap carries-well-sealing stoppers, for engagement with a separator such as-described above which operates to separate cap and base to allow the assay to proceed.

The base and cap are preferably such that the membrane-tipped pipette can be placed within a "reading well" or in a well-free position at which radiation from the pipette is accessible to the detector. Such a "reading well" may for example have a light-transparent flat base or flat side well section through which light may pass to the detector. In the case where reading is at a well-free position, this may for example be an open-ended aperture through the base or a portion of the base where its side wall is removed or recessed such that light from the pipette may reach the detector without passing through the material from which the base is formed.

The use of a "reading well" is preferred since the possibility of reagents or sample dripping into the body of the assay apparatus is reduced. Where an angled membrane is to be read, the use of a separate reading well may be avoided as simply lifting the membrane out of the liquid in a well or sucking the liquid through the membrane into the pipette leaves the membrane surface exposed for reading.

In one embodiment, the base may be formed to provide a mirror surface (e.g. a plastic prism surface) under the bottom of the reading well which reflects light from the bottom of the reading well, e.g. from the vertical to the horizontal. In this way, the detector need not be positioned below the cartridge and problems of dust or liquid falling onto the detector may be avoided. As in a Fresnel lens, a prism may similarly be produced as an integral combination of parallel individual prism elements. This prism structure is referred to herein as a "Fresnel prism", and such prisms and their uses, e.g. as light path modifiers in optical apparatus, for example assay devices, form further aspects of the present invention. Image distortion, due to surface distortion often seen in plastic mouldings with a thickness of more than few millimetres, is reduced or avoided by use of a plastic Fresnel prism rather than a conventional plastic prism having the same light incidence surface area. Thus the use of a Fresnel prism formed in the cartridge base to achieve light reflection is especially preferred in the devices of the invention. A typical "Fresnel prism", is a structure of transparent material stepped on one side and flat on the other—light incident normally on the horizontal part of a step is internally reflected by the flat surface and leaves normally through the vertical part of a step. In effect therefore it functions as a mirror. With an angled membrane however such a Fresnel prism will not generally be needed.

In the cartridges of the invention, the proximal or "open" end of at least one pipette is preferably sealed with a resilient self-sealing membrane, e.g. a rubber membrane, which may be pierced by a hollow needle to allow gas pressure application. In this embodiment, a waste reservoir is preferably disposed in the pipette between the pipette tip and the resilient membrane. With this embodiment, liquid in the cartridge may be drawn up into the waste reservoir during or at the end of assay performance so that the used cartridge may be removed and disposed of without waste leakage occurring.

The gas pressure applicator in the apparatus of the invention may for example comprise a pump, and a conduit from the pump to a cartridge attachment, and optionally at least one reservoir and a two or more position valve. Inclusion of a reservoir, e.g. of one or more litre capacity, and preferably at least two reservoirs, allows pressures above and/or below ambient to be applied to the pipette for short durations with negligible time variation of the pressure applied due to the ability to isolate the pipette from the pump and due to the relatively small pressure change within the reservoir during the pressure application period (as a result of the relatively large size of the reservoir). Between pressure applications, the pump can be used to bring the reservoir pressure back to the desired level. Since it may be desirable to vent the pipette to atmospheric and/or to provide pressures above and below ambient to the pipette, it is desirable to place a multi-position valve in the conduit upstream of the pipette to allow such different pressure applications. The valve, which should desirably also include a closed position allowing no gas flow to or from the pipette, is preferably computer operated. The use of pressure reservoirs as described above however results in a relatively large space requirement for the apparatus and device of the invention. Since the device is preferably portable, it is preferred instead to use a piston-based pump (e.g. a syringe) coupled via a conduit (preferably of minimal volume) to a cartridge attachment. Indeed it is especially preferred to have an array of coupled piston-pumps, each connected to a separate cartridge attachment so that, when the cartridge is in place, operation of a pump motor causes all of the pumps to operate. In this embodiment, the cartridge is preferably provided with blank or active means for engaging each of these attachments, the blank engaging means simply allowing the respective piston pump to vent. In certain embodiments, for example in clotting time measurements or where an analyte is required to bind to a ligand immobilized on the pipette membrane, it may be desirable to speed up or slow down passage of liquid under the influence of the pressure applicator; in these circumstances this may for example be achieved by speeding up or slowing down the speed of the pistons in the piston-pumps.

The pressure applicator is preferably coupled directly to the open end of the pipette; however alternatively and much less preferably it may be coupled directly to a well in the cartridge with the open end of the pipette open to ambient pressure.

In one particular embodiment, a (preferably moveable) pressure applicator attachment is provided for each well or well-free-reading position-of the cartridge and the cartridge is provided with blank or active means for engaging each of these attachments. In this way it may be possible to avoid the need for careful orientation of the cartridge during placement in the holder—the cartridge could be placed in any one of the pre-set permitted orientations and the lid of the apparatus closed to bring the attachments automatically into engagement with the blank and active engagement means on the cartridge. Cartridge identification (as discussed further below) by the apparatus would then allow the cartridge to be moved automatically into the correct orientation for commencement of the assay. This however is only especially desirable if it is important to reduce the time required for cartridge placement or if the cartridge is designed for use in multiple assays (i.e. has multiple pipettes).

The detector in the apparatus of the invention may be any appropriate radiation detector, e.g. a radioactive emission detector or an electromagnetic radiation detector. Alternatively the apparatus may contain two or more detectors capable of detecting different types of radiation. However, for point of care use, it is preferred that the detector be an electromagnetic radiation detector and more specifically a detector capable of detecting light in at least part of the UV to IR range, particularly the near UV to near IR range and more especially the visible range. (The term light is used here to mean electromagnetic radiation in the UV to IR range.) For this purpose it is especially preferred to use a digital camera as the detector.

The use of a digital camera as the detector is especially preferred since it can function not only as a light detector but as an image structure analyser. Thus, for example, irregularities in the image of a membrane on a pipette may be detected and corrected for.

Between detector and cartridge it may be desirable to place, movably or fixedly, items which serve either to select the radiation energy allowed to pass to the detector (e.g. filters, prisms, etc.) or to reduce stray radiation impact on the detector (e.g. apertures and light traps).

Stray radiation reducing items are especially important where the radiation to be detected is weak (e.g. resulting from chemoluminescence or fluorescence) or stimulated or results from transmission or reflection of radiation measurable by the detector. In such circumstances, light barriers or collimators may also be provided elsewhere in the apparatus or within the cartridge.

In general, the apparatus of the invention will be provided with electromagnetic radiation sources (e.g. sources of visible light or near IR to near UV), disposed to cause radiation emitted, reflected or transmitted by the desired cartridge wells or pipette to pass to the detector. As a result it is also preferred that cartridge, cartridge holder and detector be disposed in a light proof chamber in the apparatus and that the apparatus be provided with a closable access port for cartridge placement, e.g. a lid.

It is especially preferred that a light source be provided which, when the cartridge is in place, has a well between it and the detector, e.g. so that light transmittance in the well may be determined. For this purpose, the cartridge may be provided with an aperture into which such a light source may be inserted on cartridge loading, preferably an axially positioned aperture where the wells in the cartridge are disposed about a central axis.

It will be realised that the detector may be positioned relative to well and light source so as to detect transmitted, reflected, scattered or emitted light.

Where the detector is a digital camera (or a scanning laser), it may also be used for assay identification. Thus a bar-code or similar machine readable code may be placed on the assay cartridge and, reading this the computer running the apparatus can identify the nature of the assay and hence the assay steps necessary to effect. The assay user can similarly apply a bar-code or machine readable code to the assay cartridge to identify the patient so that the apparatus may generate a report identifying patient and assay or may generate an entry in or for the patient's computerized records. Code-reading and result reading systems of this nature are discussed for example in WO 98/32004.

As mentioned above, cartridges in which the pipette is capillary-tipped rather than membrane tipped may conveniently be used for assaying for coagulation time in blood or plasma (preferably blood). The pipette conveniently comprises in sequence a capillary tip, a chamber and a second capillary, which may be non-linear, e.g. sinuous, if desired. Opening the cartridge and dipping the capillary tip in a blood sample causes it to fill up to the junction with the chamber, i.e. to take up a predetermined sample volume. The cartridge may then be closed and placed in the assay device. The second capillary or one of the wells in the cartridge is coated with a clot-promoting agent (e.g. tissue factor) and the liquid sample may be contacted with this by application of sub-ambient or above ambient pressure respectively to the open end of the pipette. In the first case, the pressure causes the sample to be drawn through the chamber into the second capillary and so into contact with the clot-promoting agent. In the second case, the pressure applied expels the sample into the coated well. If desired, in this second case, the sample and clot-promoting agent may be mixed by being drawn back into the pipette and expelled again one or more times. Thereafter the sample is drawn through the capillary tip and chamber into the second capillary. In both cases, the motion of the sample in the second capillary under applied pressure is monitored by the detector until clotting has proceeded to the extent that motion is no longer detectable. This may require the sample to be shuttled back and forth in the second capillary by alternate application of below and above ambient pressures.

It will be appreciated therefore that the same capillary can be used for collecting the sample (e.g. blood), and mixing it with one or more reagents (e.g. by pumping it into and out of a well in the cartridge).

In any event, for clot time measurements it is important for the sample temperature to be controlled and thus it is desirable that the device, e.g. in the cartridge holder, be provided with temperature control, e.g. a thermostated hot-plate, a hot air source, etc.

In an alternative embodiment, clotting time in blood or plasma may be determined by depositing the sample into a well containing an effervescent agent and monitoring the rate of rise of the bubbles generated using a digital camera.

Where a capillary tipped pipette is used, it may be desirable for this to be provided separate from the cartridge, formed to be positionable in a well and couplable to the pressure applicator.

Such capillary-tipped pipettes and their use in conjunction with assay cartridges form further aspects of the invention.

Thus viewed from a further aspect the invention provides an assay apparatus comprising:

i) an assay cartridge comprising at least one, and preferably at least two, wells and a pipette positionable in at least one, and preferably at least two, of said wells, said pipette having a capillary tip;

ii) a holder arranged to receive said cartridge;

iii) drive means operable to position said pipette in selected wells of said cartridge;

iv) a gas pressure applicator couplable to said pipette whereby to cause liquid flow through said membrane; and v) a radiation detector operable to detect radiation from a well of said cartridge or from said pipette. Viewed from a still further aspect the invention also provides an assay cartridge comprising at least one, and preferably at least two, wells and a pipette positionable in at least one, and preferably at least two, of said wells, said pipette having a capillary tip.

Using the pipettes in the assay cartridges of the invention, it is thus possible to introduce test samples into cartridge wells, to mix reagents or reagents and sample in the wells, to transfer liquids from one well to another, etc. By pumping liquids in and out of a pipette in one well it is possible to improve homogeneity of mixing and by pumping liquids back and forth across a reagent-carrying pipette membrane it is possible to increase the extent of the reaction with the reagent. By varying the-rate at which a liquid is pumped across a reagent-carrying pipette membrane it is also possible to vary the extent to which the reagent reacts. Accordingly the pipette and cartridge format gives great versatility for assay performance.

Where the assay cartridge includes a capillary tipped pipette, e.g. for conveying blood samples, it is frequently desirable to remove excess fluid from the outer surface of the capillary. In such cases, it is preferred that one of the wells be provided with an absorbent pipette wiper against which the capillary tip may be drawn so as to cause the wiper to absorb any fluid on the outer surface of the capillary. This wiper may for example take the form of an absorbent pad disposed at or near the upper end of the well, e.g. a U shaped pad, preferably notched at the base of the U. In such an embodiment, as the capillary is withdrawn from the well it may be displaced sideways to engage the capillary tip with the notch. Since such displacement may occur before the membrane-tipped pipette is fully withdrawn from the well in which it is disposed, it may be necessary to design the wells to prevent the membrane-tipped pipette from being driven into a well side wall. Thus the well for the membrane tipped pipette may be made wider or alternatively its side wall may be partially removed at the upper end of the well.

Rather than wiping a capillary tip to remove excess sample from the outside of the tip, an alternative is to insert the capillary tip into an absorbent array disposed parallel with the axis of the capillary tip, e.g. absorbent fibres lying parallel to the tip or sheets of absorbent material (e.g. paper) with surfaces parallel to the capillary tip axis. Since the open tip of the capillary will not contact the absorbent material, the contents of the capillary are not removed while the outside of the capillary is cleared of excess fluid. This is particularly important with blood samples. Thus for example a 1 µL capillary shows poor precision unless the blood sticking to the outside of the capillary is removed. On an average a 1 µL capillary carries 0.25 µL on the outside. Without removal of blood sticking to the outside a CV (coefficient of variation) of about 7-8% (volume of blood delivered) is found. With efficient removal of blood carried on the outside the CV is reduced to 1.0-1.5%.

Where capillary wiping takes place as part of assay performance, the time delay before wiping occurs may lead to drying of the blood on the outside of the capillary. When this happens the blood will not all be absorbed and may be solubilized during a subsequent dilution step. If the user waits one minute from taking the blood into the capillary to starting the instrument, the wiping off is somewhat inefficient. Waiting three minutes means no absorption of blood at all.

It is therefore greatly preferable if capillary wiping takes place immediately after blood sample uptake by the capillary. This can be achieved by disposing in a capillary-receiving well of the cartridge an absorbent array as described above, e.g. a strip of paper folded into a V-shape with the open end of the V receiving the capillary tip. The paper may be positioned and kept stable in the well either by using the forces of the paper pushing outwards against the well walls or if necessary by mounting the paper in a supporting frame. When the user introduces the capillary holder into the cartridge, the capillary will push the two upper arms apart and the capillary will slide down in contact with the paper on two sides opposite to each other. This construction with the paper parallel to the capillary ensures that no blood can be absorbed from the interior of the capillary and in addition the capillary will never hit the bottom part of the folded paper. Using a 1 µL capillary and whole blood, a CV (blood volume) of 0.75% was achieved with this construction.

In a further preferred embodiment, the assay cartridge is provided to the user with a capillary-tipped pipette to be used for sample taking either loose or detachably mounted in the cartridge, e.g. in an end well of a linear well array. In this embodiment, detachably mounted on the capillary tip, i.e. the distal end of the pipette, is a sleeve which closely engages and is preferably flush with the open end of the capillary-tip. On sample uptake by the capillary, any excess external liquid accordingly sticks to the outside of the sleeve rather than to the outside of the capillary proper. The sleeve is preferably provided, e.g. on its external surface, with means to engage with the inner or upper surface of a well in the cartridge (e.g. a distortable flange, etc.) so that when the loaded capillary-tipped pipette is pressed into that well the capillary-tipped pipette can then be removed from the well (e.g. on commencement of automated assay performance) leaving the sleeve and the excess external liquid behind in the well. Experiments have shown that, in transferring a 1 µL blood sample using such a sleeve protected capillary, CV (blood volume) as low as those achievable with the folded paper wiper described in the previous paragraph can be achieved.

For certain assays, it may be desirable to carry out a separation of the sample, e.g. to generate a plasma sample from an original blood sample. In such cases it may be desirable to place a filter in one of the wells. This may be removable or alternatively may form part of an integral pipette extension seated in the well. Such a pipette extension may for example comprise a cylinder open at its upper end where it is shaped for engagement with a pipette mounted on the cartridge cap, and packed at its lower end with glass fibre. In one such embodiment, the sample may be taken up into a capillary tipped pipette mounted on the cartridge cap when cap and base are separated or into a capillary tipped pipette mountable in the cartridge cap. Then, with the cap and base engaged, the sample may be expelled under air pressure into the cylinder of the pipette extension; the filtrate will pass into the base of the well. A second cap-mounted capillary tipped pipette can then be used to draw up the filtrate after the pipette and pipette extension have been withdrawn from the well. In this way, starting from a blood sample, an undiluted plasma sample may be produced.

As well as pipette extensions, capillary wipers, etc., other items may be disposed within the wells of the cartridge. Thus for example the well for receiving a sampling capillary may contain a further fixed or removeable well containing a dried reagent so that the sample and this reagent may be mixed at the onset of assay performance.

The apparatus, device and cartridges of the invention are for use in assay methods. Such methods, using the apparatus, device or cartridges of the invention form a further aspects of the invention. While the invention is particularly suited for medical diagnostic assays, it can also be used for other assays, e.g. environmental, nutritional, etc., including assays of samples from manufacturing processes. It is particularly suitable for such uses as the cartridges and devices can be produced sufficiently small as to be fully portable, e.g. with the maximum dimension of the device (excluding any connectors to external equipment or power sources) being no more than 30 cm, more preferably no more than 20 cm.

The use of membrane-tipped pipettes in assays is also novel and forms a further aspect of the invention. Viewed from this aspect the invention provides an assay method wherein a liquid is transferred from a container into a pipette, characterised in that the end of said pipette through which liquid enters is sealed by a liquid permeable membrane.

Viewed from another aspect the invention also provides the use of the apparatus of the invention to assay for an analyte in a biological sample or for a property of a biological sample, e.g. to assay for clotting time in a blood or blood-derived sample or to assay for a protein analyte in a body fluid or body fluid-derived sample.

Documents referred to herein are incorporated herein by reference.

Examples of apparatus and methods according to the invention will now be illustrated further with reference to the following non-limiting Examples and the accompanying drawings, in which:—

Figure 1:
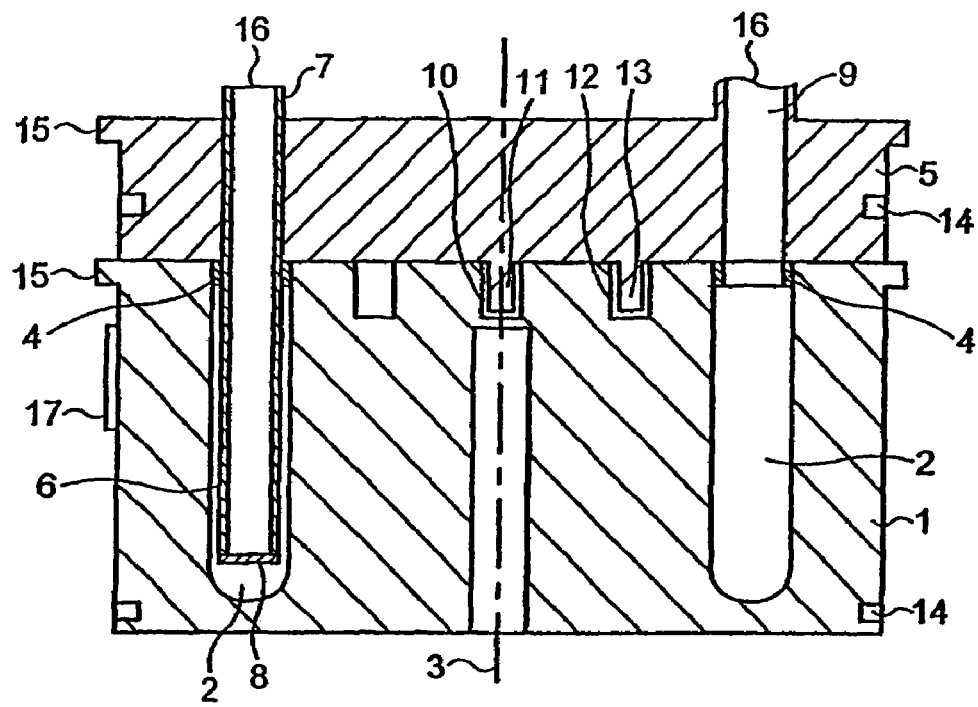
FIG. 1 is a schematic cross-section through a cartridge according to the invention.

Referring to FIG. 1, there is shown a transparent plastic cylindrical cartridge base 1 containing cylindrical wells 2 (only two of which are shown) disposed in a circular array about cartridge axis 3. Above cartridge base 1 is disposed cartridge cover 5. The mouths of each well are sealed by stoppers 4 attached to the cover 5. Cover 5 also holds pipette 6, presenting a pressure applicator attachment extension 7 to the outside of the cover and with membrane 8—tipped pipette end disposed in a well 2 of the base 1. A sample introduction port 9 is also present in the cover 5. Port 9 and pipette 6 are kept in registry with wells 2 by mating projections and recesses 10, 11, 12, 13. Similar mating projections and/or recesses 14 (here shown as recesses) are provided in base 1 and cover 5 to allow base and cover to engage with cartridge holder and drive means (not shown) of the assay apparatus. Base and cover are provided with flanges 15 to engage with the separator (not shown) which pushes base and cover seals 16 apart before assay performance begins. The nature of the assay for which the cartridge is intended is identified by a bar-code label 17 on the side of the base. The pipette and sample application port are shown sealed by removable strip seals 16. These are removed before the cartridge is used.

Figure 2:
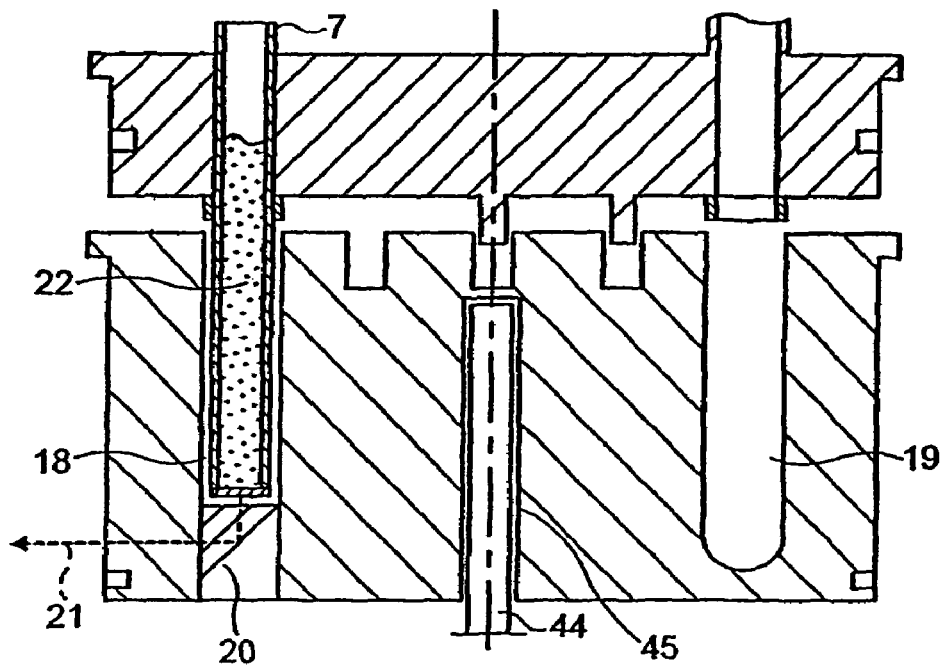
FIG. 2 is a schematic partial cross-section through a cartridge according to the invention.

In FIG. 2, the cartridge of FIG. 1 is shown in a different orientation for assay result reading at the end of assay performance. In this orientation, the wells 18 and 19 shown are different from the wells 2 in FIG. 1. Well 18 is a "reading well" having a plastic prism 20 placed at its base and part of the light path from membrane to detector is shown as a dotted line 21. Pipette 7 is shown as containing used reagent 22. Light source 44 is shown in place inside axial channel 45 in the cartridge base.

Figure 3:
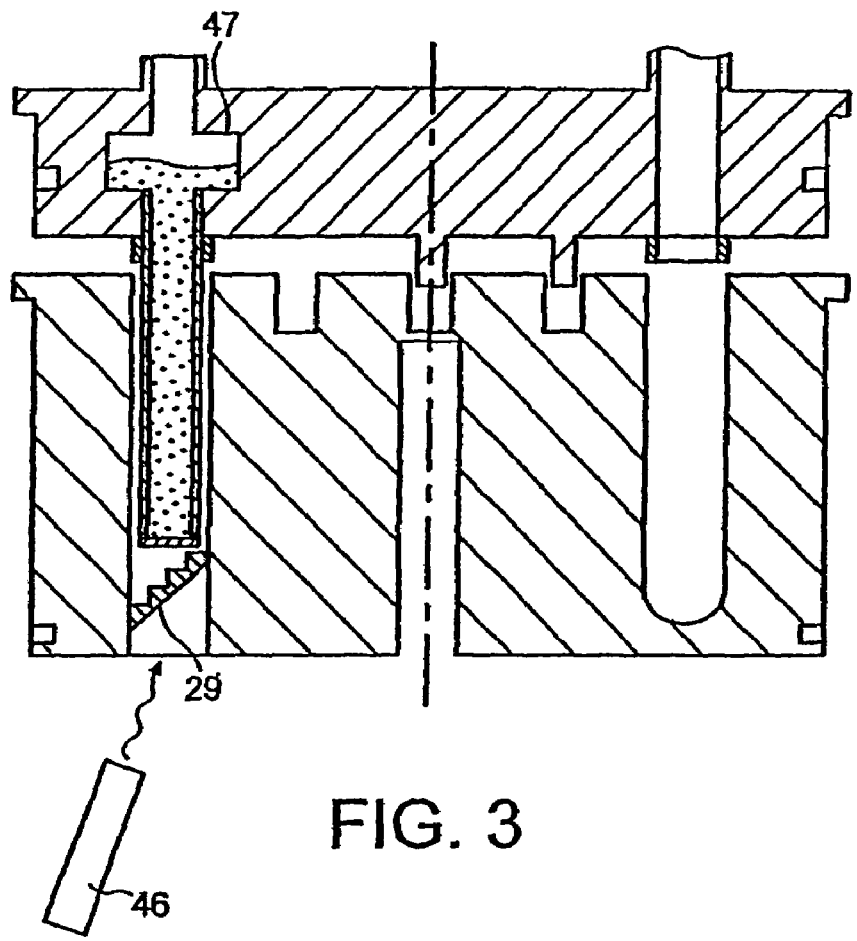
FIG. 3 is a schematic partial cross-section through a cartridge according to the invention.

In FIG. 3 is shown a different embodiment of the cartridge of FIG. 2 in which the bottom of reading well 18 is stepped and the base below reading well 18 is inclined whereby together to form a Fresnel prism 29. Light source 46 is arranged to illuminate the membrane. In this embodiment, the pipette 7 is also shown with a relatively large volume chamber 47. This facilitates retention of the liquids used in the assay in the pipette.

Figure 4:
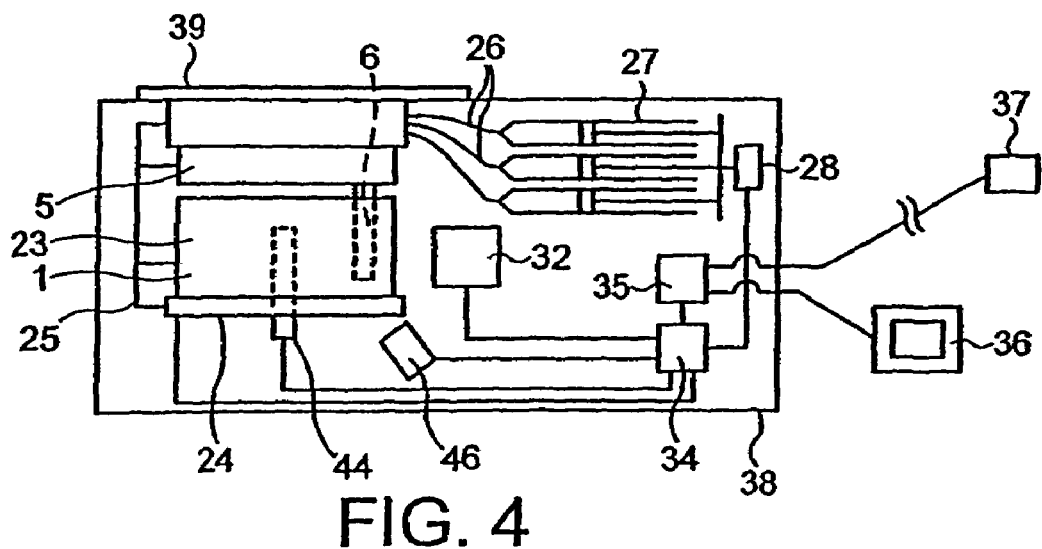
FIG. 4 is a schematic drawing of apparatus according to the invention.

In FIG. 4 the components of the apparatus of the invention are shown schematically. Cartridge 23 (with base 1, cover 5 and pipette 6) is held by holder 24 and moved by drive means 25. Pipette 6 is connected via conduits 26 to piston pumps 27 driven by motor 28. A detector, a digital camera 32, is arranged to detect light from the reading well of cartridge 23 when the assay is completed and light sources 44 and 46 with power supply 34 are arranged to illuminate the reading well.

Drive means 25, motor 28, camera 32 and power source 34 are operated by computer 35 which provides an output on monitor/printout 36 or to remote computer 37 (e.g. via an infra-red wireless connection). Camera 32, light sources 44 and 46, holder 24 and cartridge 23 are within a light-tight chamber 38 provided with a cartridge loading and unloading port 39.

Figure 5:
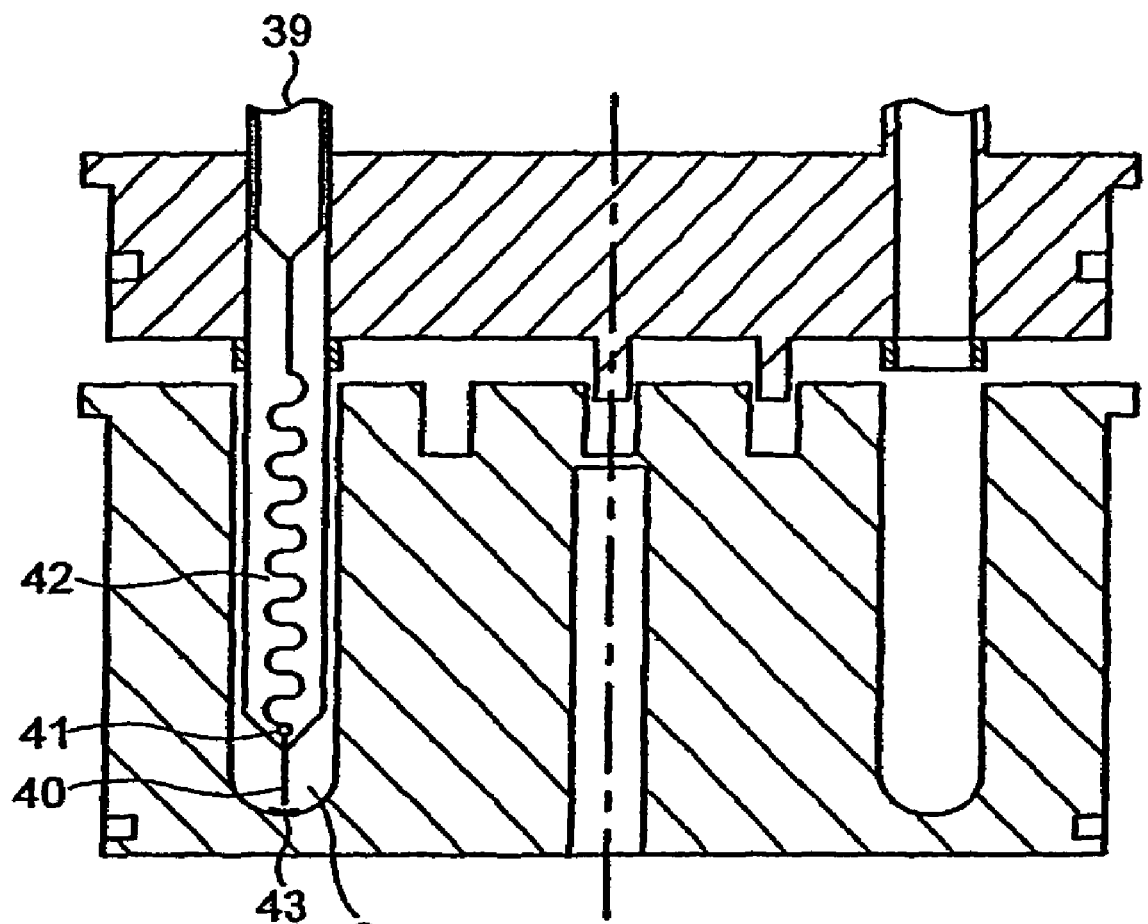
FIG. 5 is a schematic cross-section through a cartridge according to the invention.

FIG. 5 shows a cross-section through an alternative, capillary-tipped pipette usable in the cartridges of the invention.

Open pipette-end 39 is adapted to be attached to the pressure applicator. The other pipette end is provided with a capillary tip 40 which communicates to chamber 41 and thence via a further sinuous capillary 42 to open-end 39. Part 43 of the base of well 2 is coated with a coagulation promoting agent, e.g. tissue factor. Dipping the capillary tip 40 into blood or plasma causes a fixed volume sample to be drawn in by capillary action. Withdrawing the pipette from the sample and then either expelling the content into the clot-promoting agent coated well and then sucking the sample back into the capillary or sucking the sample past the tissue factor in the capillary, hastens onset of clotting and the digital camera can be used to determine the time at which sample flow along capillary 42 effectively ceases, i.e. the clotting time.

FIGS. 9 to 19 showed alternative arrangements for an assay cartridge in which the wells are arranged in a linear way.

Figure 9:
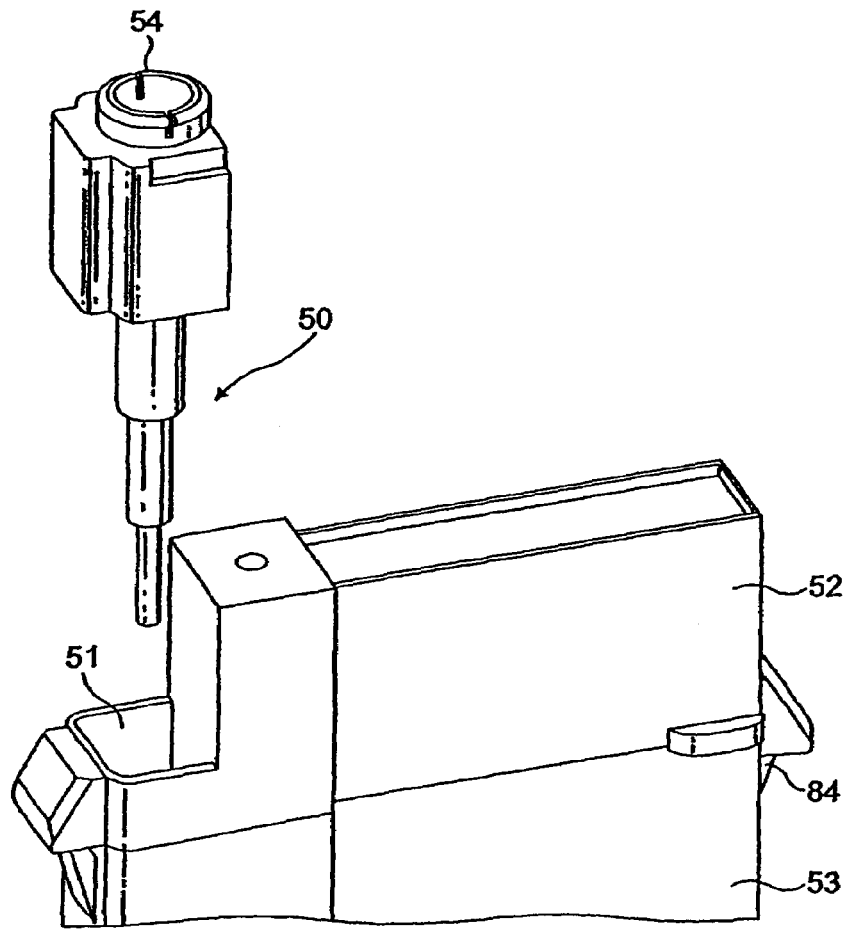
FIGS. 9 to 19 are schematic views of further embodiments of cartridges according to the invention in which the wells are arranged in a linear array.
Figure 10:
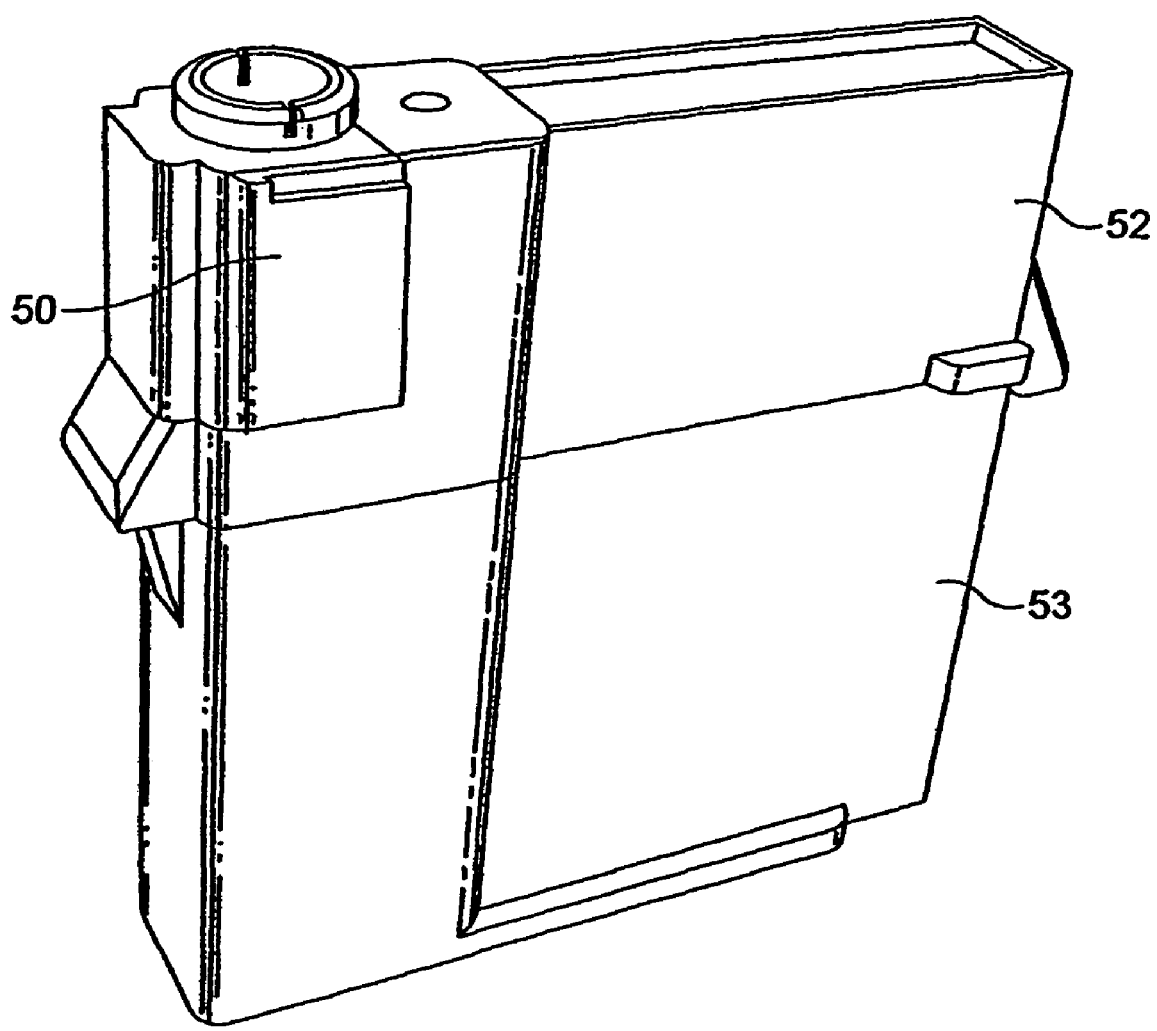

FIG. 9 shows a detached capillary tipped pipette 50 which may be dipped into a liquid to take up a sample. The loaded pipette may then be slotted into aperture 51 in cartridge cap 52 so disposing the capillary tip in an end well in cartridge base 53. The open upper end of pipette 50 is provided with notches 54 so that if the operator engages the pipette with the cartridge cap and base by pressing on the top of the pipette this does not raise the pressure in the pipette and so expel some or all of the sample prematurely. FIG. 10 shows the cartridge of FIG. 9 assembled following insertion of the sampling pipette, i.e. at the stage when the cartridge is ready to be placed in the apparatus of the invention.

Figure 11:
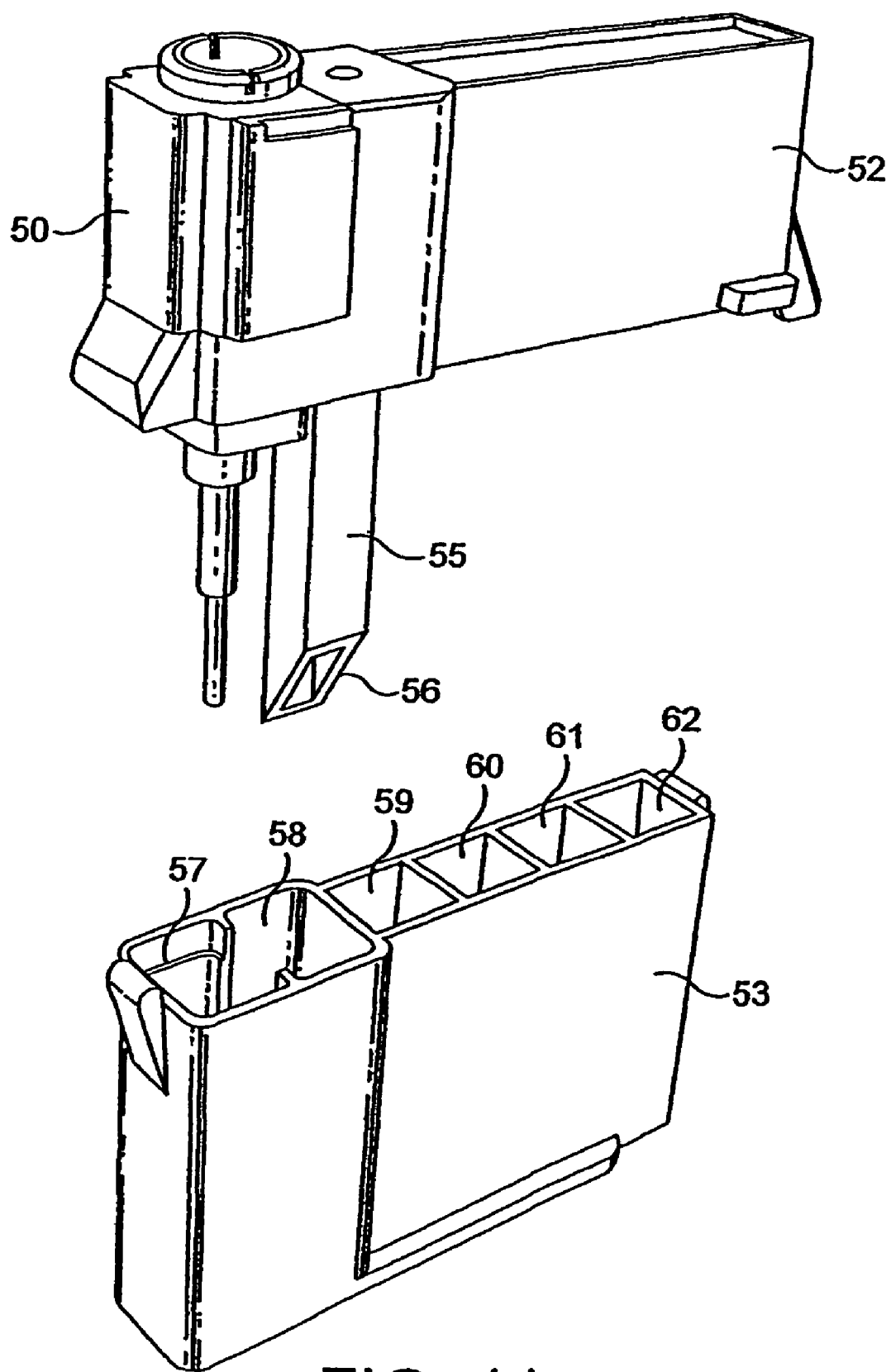
Figure 12:
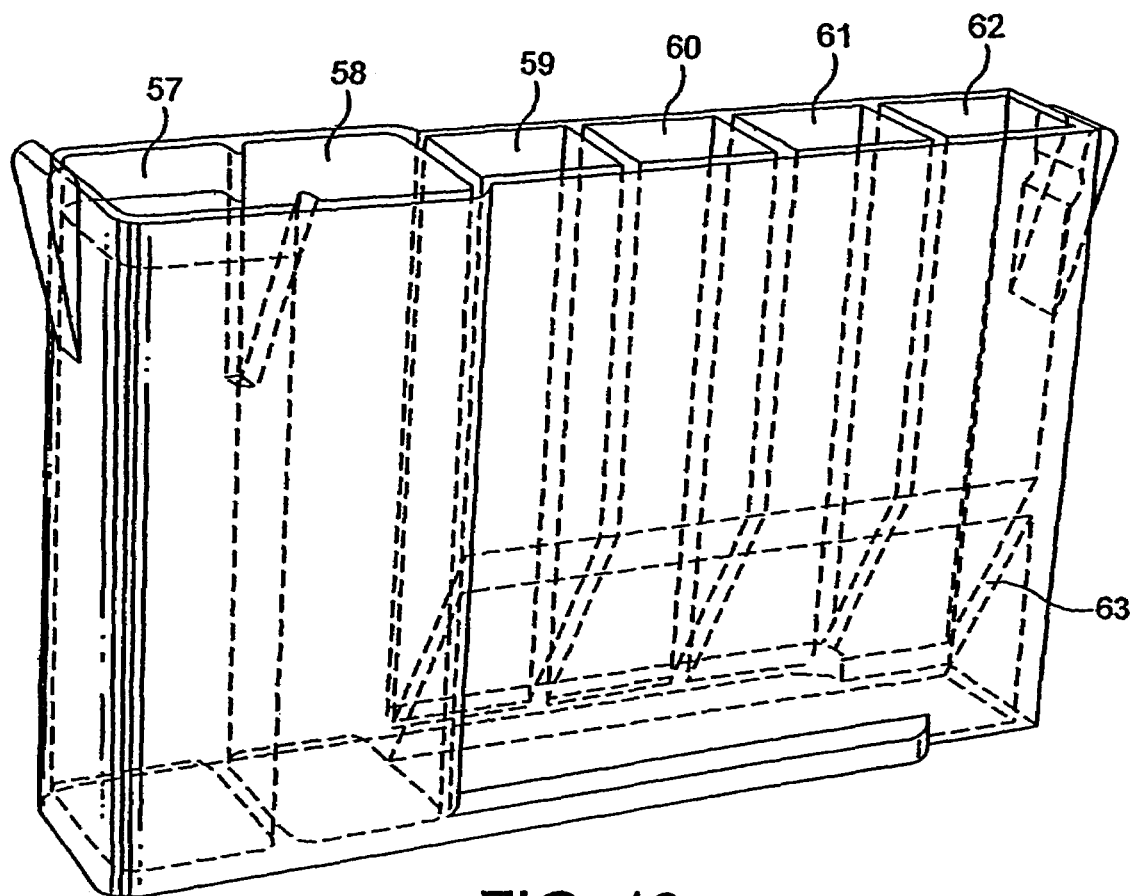
Figure 13:
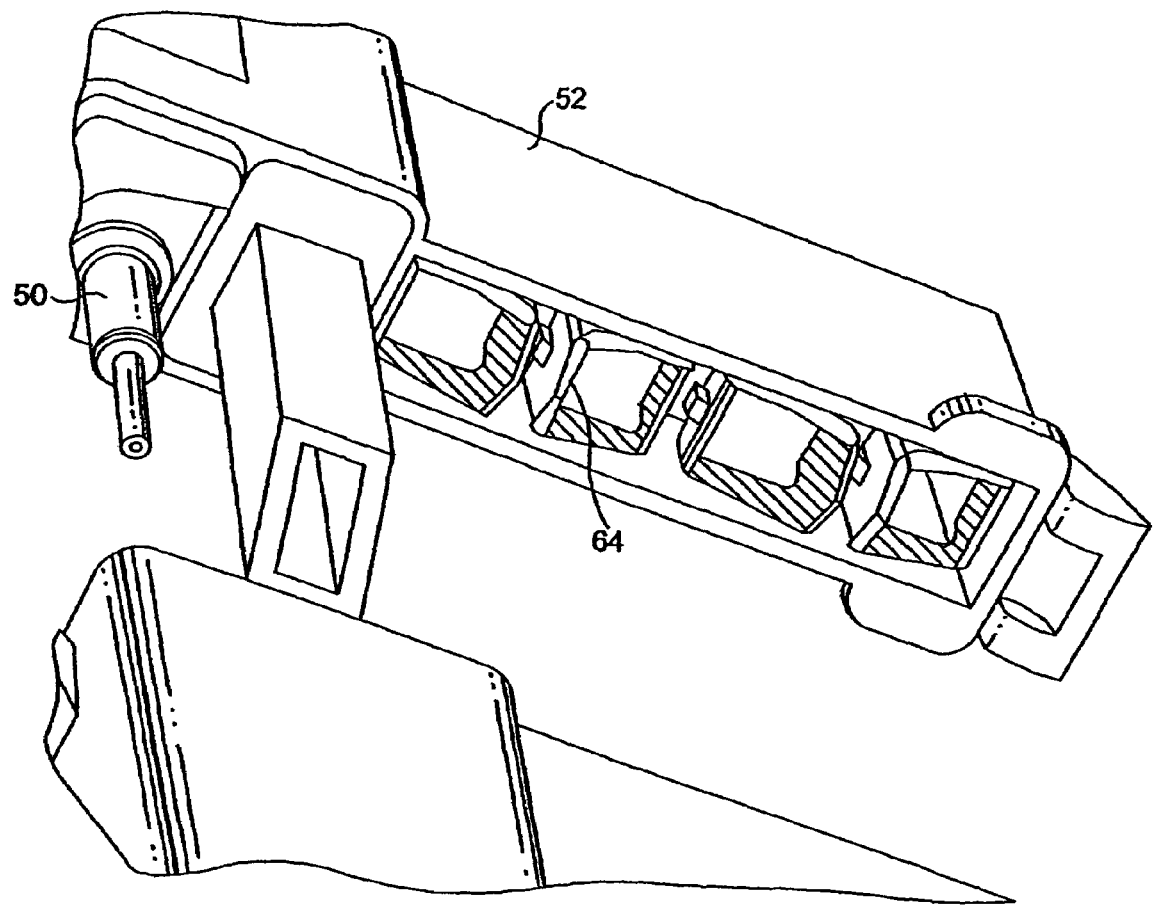
Figure 14:
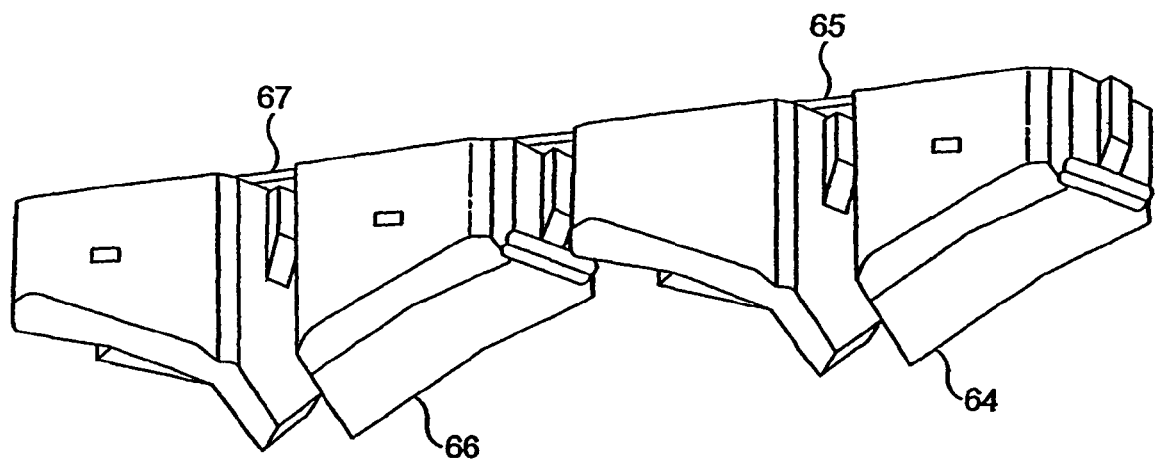
Figure 15:
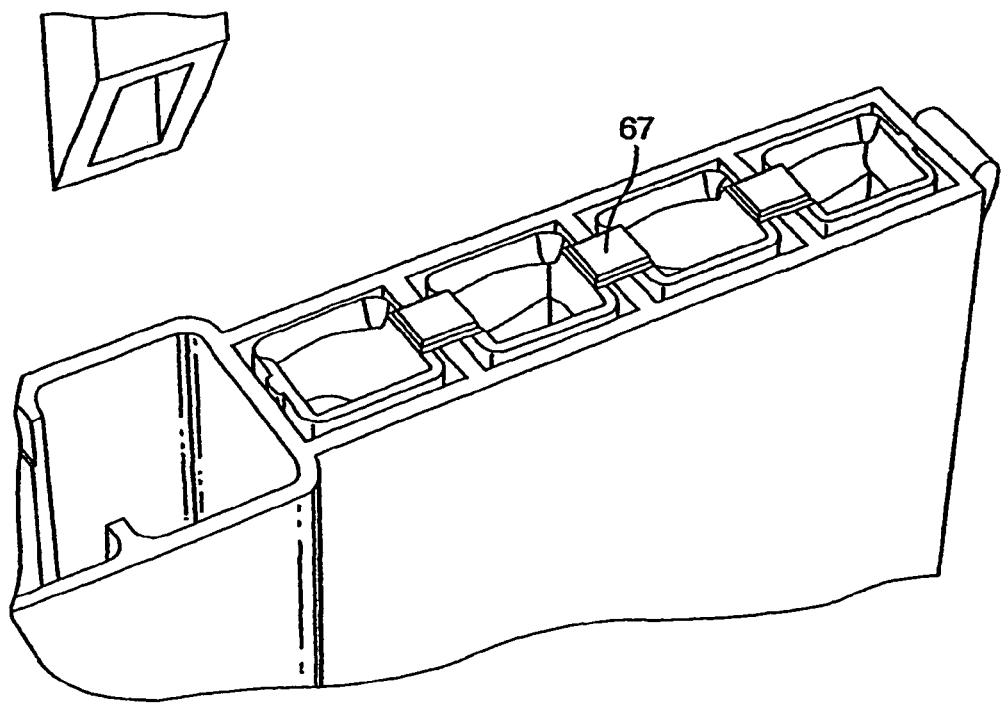

During performance of the assay, cartridge cap and base will be separated by disengagement of latch mechanism 84. The separated cartridge is shown in FIG. 11. Cartridge cap 52 is shown carrying capillary tipped pipette 50 and membrane tipped pipette 55. Membrane tipped pipette 55 is rectangular in cross-section and has an angled tip 56. For clarity, the membrane covering the open lower end of pipette 55 is not shown. Cartridge base 53 is shown with six wells 57-62, all generally rectangular in cross section. To allow for capillary tip wiping, a portion of the upper section of the wall between wells 57 and 58 is absent. As shown in FIG. 12, the bases 63 of wells 59 to 62 are angled so as to be parallel to the tip 56 of the membrane-tipped pipette. Wells 59 to 62 are foil-sealed at their upper ends. The foil seals are pierced during assay performance by piercers 64 initially mounted in the cartridge cap (see FIG. 13). The individual piercers are connected together in a strip 65 shown in FIG. 14. Each piercer, which may be metal but preferably is plastic, is a hollow rectangular cross-section cylinder with a blade edge 66 on the lower rim and flanges 67 on the upper rim which cause the piercer to be retained by the cartridge base once it has been forced into engagement with the base (as shown in FIG. 15). The internal cross section of the piercers is shaped to act as a guide for the pipettes.

Figure 16:
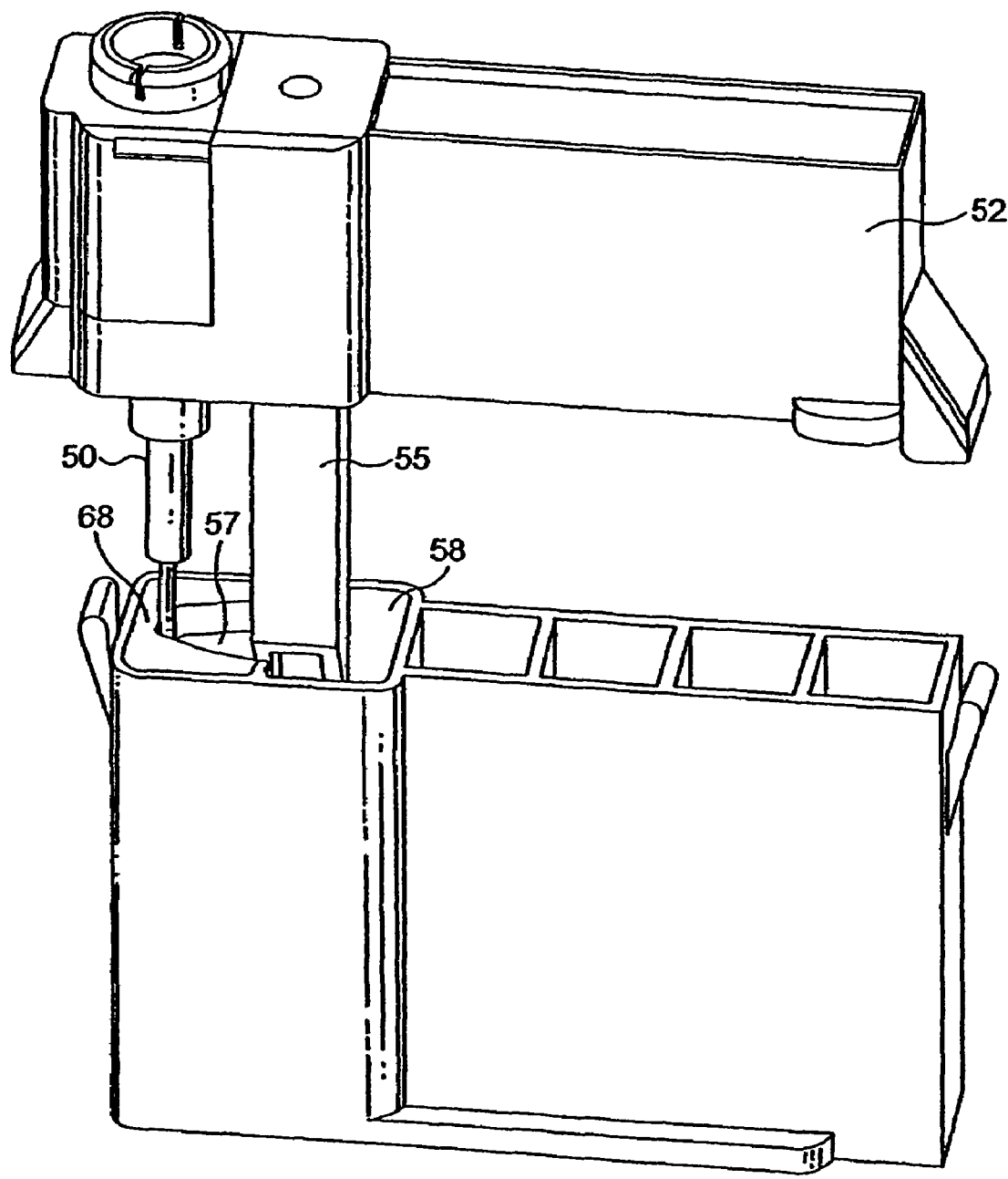

FIG. 16 shows the cartridge cap and base being separated with a sideways displacement to bring the capillary tip of pipette 50 into contact with an absorbent wiper 68 disposed at the top of well 57. As shown, membrane-tipped pipette 55 is partly displaced from well 58 into well 57.

Figure 17:
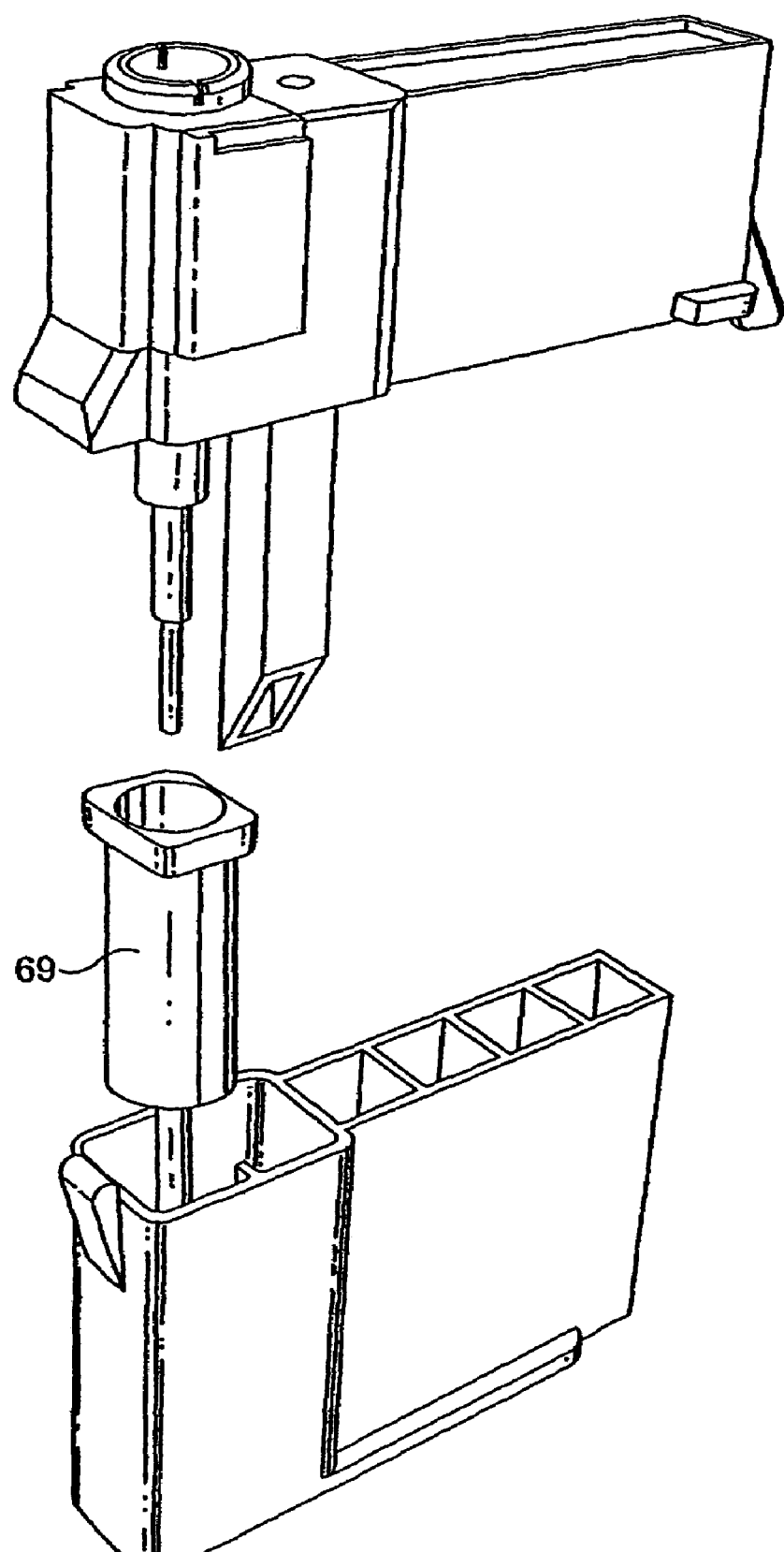
Figure 18:
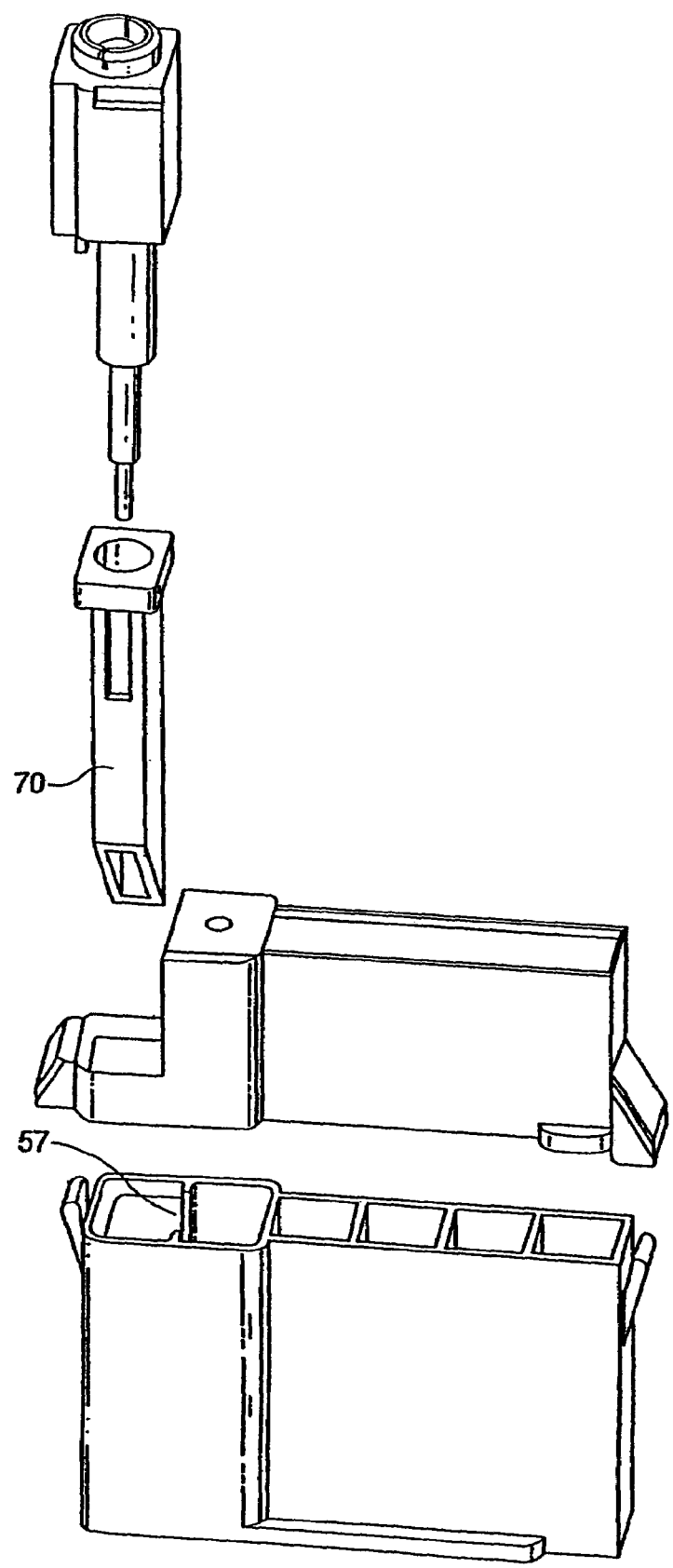

FIGS. 17 and 18 are exploded views of cartridge cap and base assemblies with pipette extensions 69 and 70 which in use would be disposed in the well (57) into which the sampling pipette 50 is initially introduced. In the case of FIG. 18, the pipette extension 70 serves to transform the sampling pipette into a membrane tipped pipette, e.g. to allow a sample to be filtered.

Figure 19:
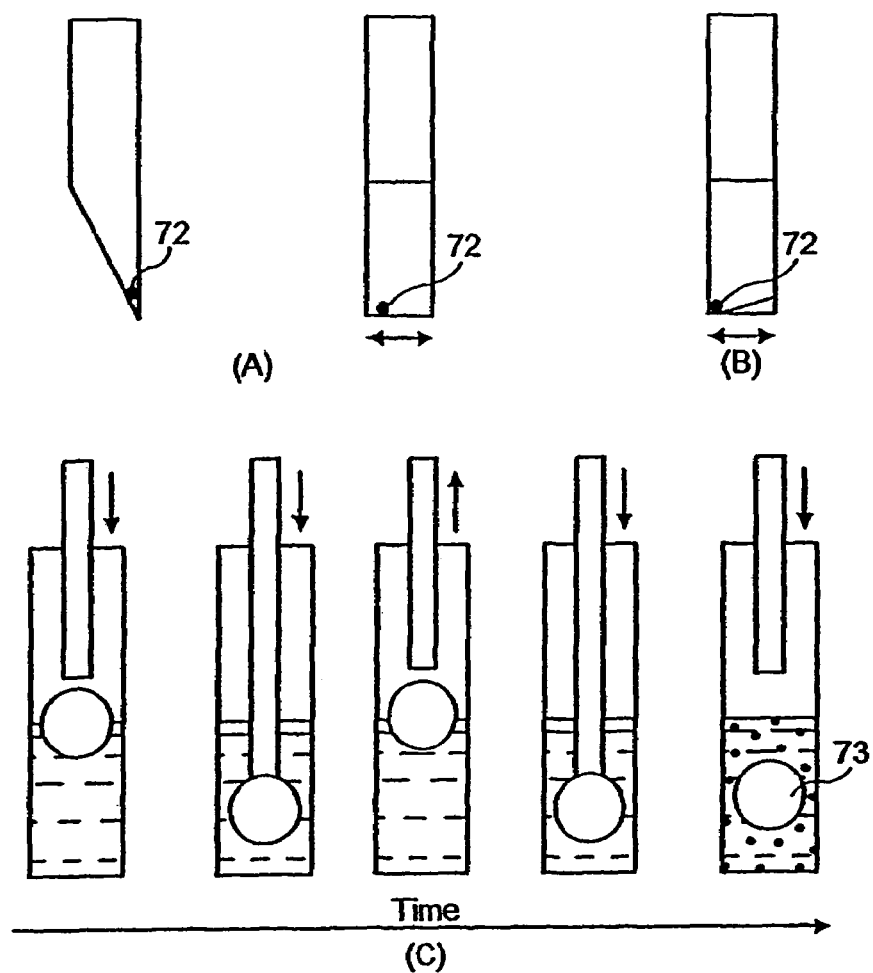

FIG. 19 shows the lower ends of three wells arranged for performance of blood clotting assays having in FIGS. 19a and 19b a steel ball 72 movable along the base of the well and in FIG. 19c a polymer ball 73 which will float on the sample surface while it is still fluid.

After assay performance using the cartridges of FIGS. 9 to 19, an absorbent strip is preferably inserted into aperture 71 in the cartridge cap so as to prevent seepage of any fluid remaining in wells 58 to 62. Alternatively, the aperture may be sealed with an elongate "piston" which is used to press the piercers through the foil seals of wells 58 to 62.

Figure 20:
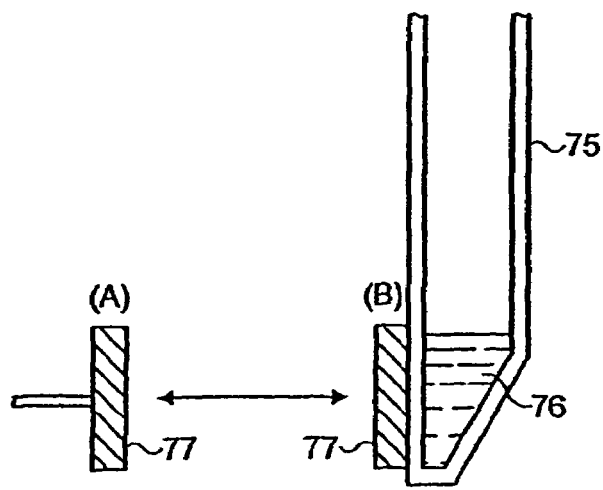
FIG. 20 is a schematic view showing how a movable magnet may be used to separate magnetic polymer beads from a sample in a well of a cartridge according to the invention.

In FIG. 20, is shown a well 75 in a cartridge according to the invention. This well contains a liquid 76 containing magnetic polymer beads. To separate the beads from the liquid during assay performance (e.g. as in Example 12 below), a magnet 77 is moved from a position (A) in which it is remote from the well to a position (B) in which it contacts the well wall. A membrane-tipped pipette can then be inserted into the well and used to withdraw the liquid leaving behind the magnetic beads.

Figure 21:
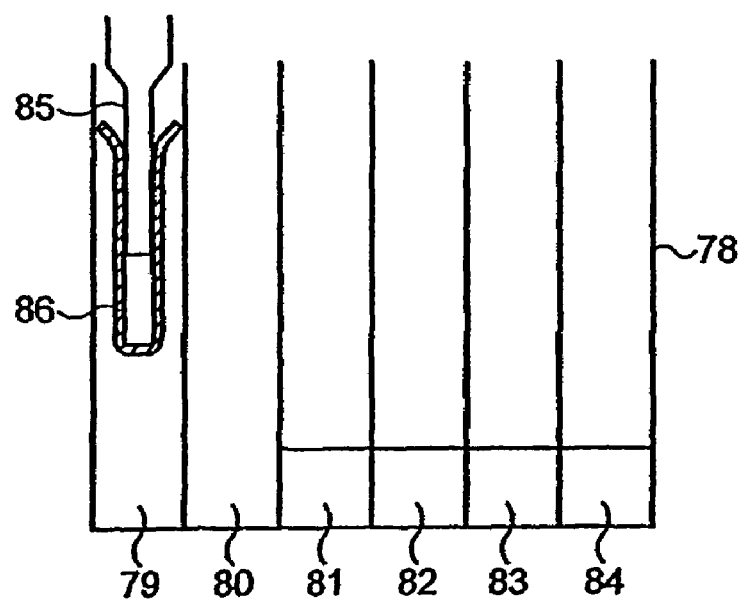
FIG. 21 is a schematic view showing how a paper strip may be used to wipe excess liquid off the outside of a capillary-tipped pipette in a cartridge according to the invention.

In FIG. 21, is shown schematically a cartridge 78 according to the invention with a linear array of wells 79-84, an end one 79 of which is arranged to receive a sampling capillary the tip 85 of which is shown. Within well 79 is disposed a V-shaped fold of absorbent paper 86 such that insertion of capillary tip 85 into well 79 causes the sides of the capillary to be wiped.

In FIG. 22A-D, is shown partially and schematically a cartridge 87 according to the invention having capillary-tipped and membrane-tipped pipettes 88 and 89 in cartridge cap 90. The membrane-tipped pipette 89 has towards its proximal end a liquid waste reservoir 91 and when in place within cartridge cap 90 the reservoir is closed by a self-sealing rubber gasket 92. Where pressure is to be applied to the proximal end of the membrane-tipped pipette 89 this is done by piercing the gasket 92 with a hollow needle 93 attached to a pressure applicator (not shown).

Figure 23:
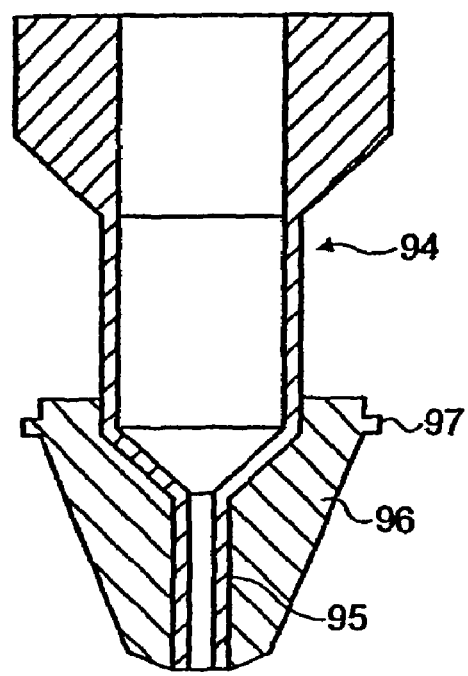
FIG. 23 is a schematic cross-sectional side view of a capillary-tipped pipette for use in an assay cartridge according to the invention.
Figure 22A:
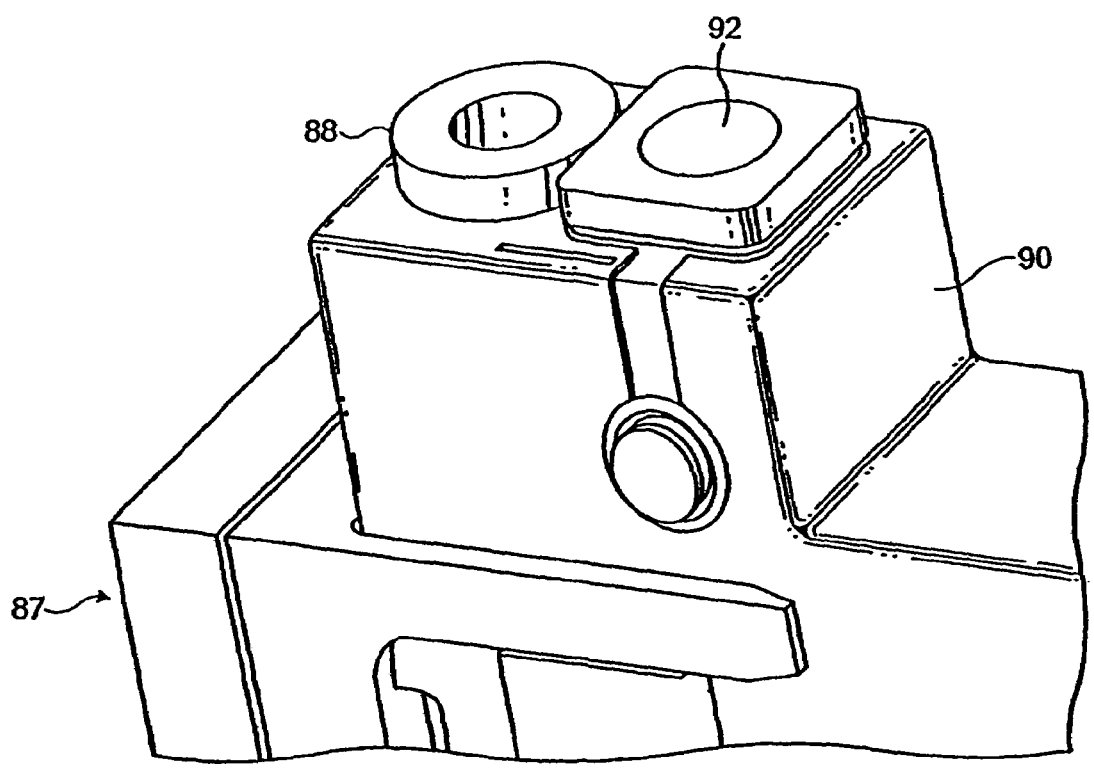
FIG. 22 is a schematic view showing how a membrane sealed waste reservoir may form part of a pipette in a cartridge according to the invention.
Figure 22B:
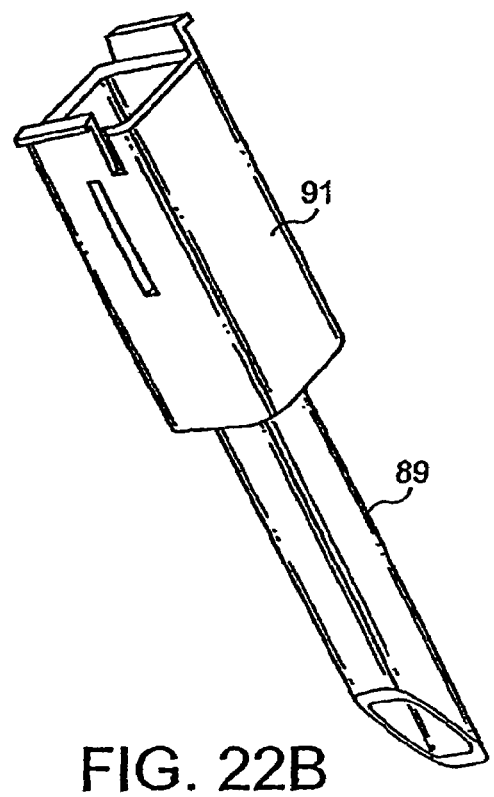
Figure 22C:
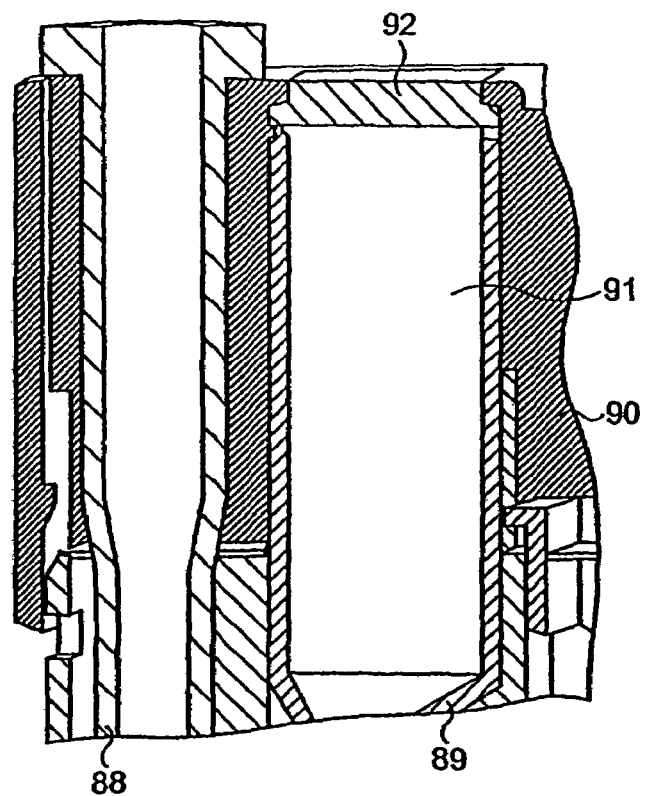
Figure 22D:
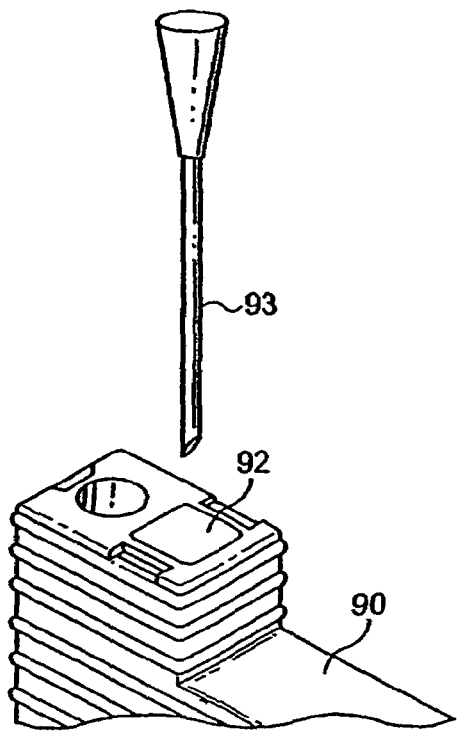

In FIG. 23 is shown a capillary-tipped pipette 94 which is provided as part of an assay cartridge according to the invention. As provided to the user, pipette 94 is loosely positioned in one well, e.g. as pipette 50 in well 57 in the embodiment of FIG. 11. The distal end 95 of pipette 94 is provided with a sleeve 96 which grips the pipette end and closely surrounds and is flush with the very tip of the capillary. The upper rim of sleeve 96 is provided with a distortable flange 97 which can be forced past a matching flange in the well so as to lock the sleeve into the well. In use, the capillary-tipped pipette is removed from the cartridge with sleeve 96 attached, dipped into a liquid sample to take liquid into the capillary tip, and replaced in the well and pressed to lock the sleeve into the well. The cartridge may then be loaded into the assay device and in assay operation separation of cartridge cap and base serves to disengage the sleeve from the capillary.

EXAMPLE 1

Assay for C-reactive Protein in Serum

1 µl samples of human blood, spiked with purified C-reactive protein (CRP) to concentrations ranging from 0 to 160 mg/l are placed in a 9 mm internal diameter, round-bottomed well (in an assay cartridge equivalent to the cartridge of FIG. 1) containing 200 µL of an aqueous dilution liquid (30 mM borate buffer, pH 8.0 containing 0.01% w/v sodium citrate, 0.02% w/v $NaN_3$ and deoxycholate).

The membrane-tipped pipette, having an external diameter of 7.2 mm, is lowered into the sample-containing well, and below ambient pressure is applied to the open end of the pipette causing the well contents to flow through the membrane into the pipette. In this Example, the pipette membrane is a nitrocellulose sheet having immobilized thereon a monoclonal anti-CRP antibody (prepared by conventional techniques).

The pipette is then removed from the well and lowered into a second well of the same configuration containing 200 µL of an aqueous dispersion of gold microbeads (average diameter 4.5 nm, concentration (optical density at 540 nm) of about 3, corresponding to an antibody concentration of about 50 µg/mL in 50 mM borate buffer pH 8.05, containing 20 mM NaCl, 0.05% w/v $NaN_3$ and 0.1% w/v BSA) conjugated in conventional fashion to a monoclonal anti-CRP antibody. Below ambient pressure is again applied to the open end of the pipette causing the liquid in the well to pass into the pipette so saturating the membrane with the gold conjugate.

The pipette is then removed from the second well and lowered into a third well, again of the same configuration, containing 200 µL of the aqueous dilution liquid (supra) Below ambient pressure is applied to the open end of the pipette to draw the washing reagent into the pipette; in this way, unbound gold conjugate is removed from the membrane.

The pipette is then removed from the third well and placed into a fourth, 9 mm internal diameter, flat-bottomed, empty well. For this assay, this fourth well is the reading well. The pipette membrane is illuminated (e.g. with green light from a LED) through the transparent well-containing base of the assay cartridge and light of 540 nm reflected by the membrane is detected using a detector (e.g. a digital camera or a photodiode).

Figure 6:
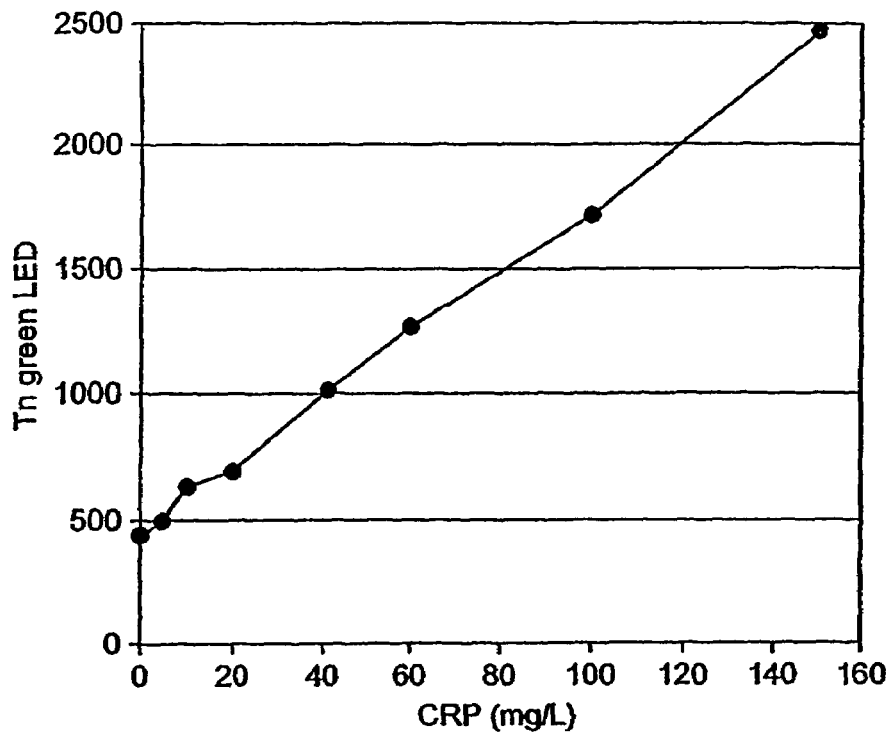
FIGS. 6 and 7 show dose-response curves for the assays of Examples 1 and 2.

FIG. 6 of the accompanying drawings shows the linear dose-response for this assay using a green LED.

Performance of the assay requires about 40 seconds from serum addition to reflectance determination.

EXAMPLE 2

Assay for Human Serum Albumin in Urine

Human urine is depleted of human serum albumin (HSA) by ultrafiltration and then spiked with purified HSA to concentrations between 0 and 200 mg/L.

A 10 µL sample of the urine is transferred in a capillary into a 9 mm internal diameter, round-bottomed well (in an assay cartridge equivalent to the cartridge of FIG. 1) containing 200 µL of aqueous sodium phosphate buffer, pH 5.6 containing 4.0% v/v propan-1-ol, 0.05% w/v $NaN_3$, 0.003% w/v Tropeolin-O and 0.5% w/v BSA. The urine is mixed with the dilution buffer by being pumped in and out of the capillary three times. The capillary is removed and the membrane-tipped pipette is lowered into the well. In this assay the membrane is a nitrocellulose sheet having immobilized thereon a monoclonal anti-HSA antibody. The diluted sample is drawn into the pipette as in Example 1.

The pipette is then removed from the well and lowered into a second well having the same configuration but containing 200 µL of a dispersion of gold microbead-antibody conjugate (as in Example 1 but with an anti-HSA rather than an anti-CRP antibody, 50 mM borate buffer pH 7.8, 0.05% w/v $NaN_3$, and 0.2% w/v BSA). The well contents are drawn into the pipette as in Example 1, and as in Example 1 the pipette is then transferred to a third (washing) and fourth (reading) well. In this assay the washing reagent is PBS, pH 7.4.

Figure 7:
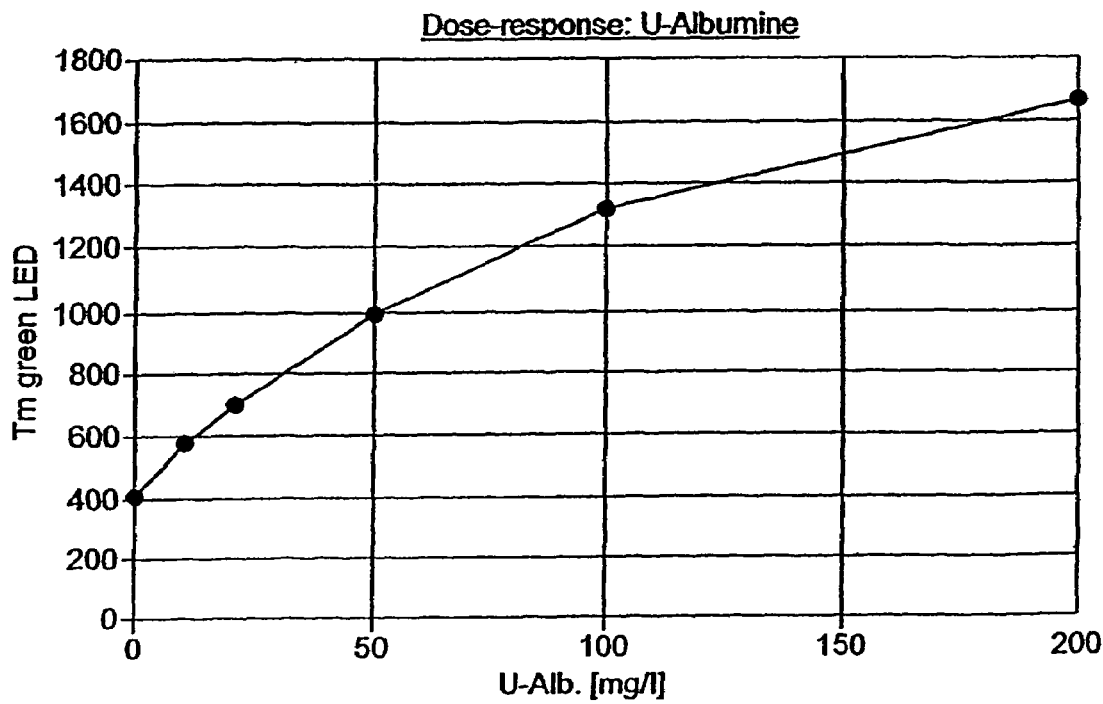

FIG. 7 of the accompanying drawings shows the dose-response curve for this assay.

EXAMPLE 3

Assay for Glycated Hemoglobin in Blood

1 µL of whole blood is taken from a blood sample using a capillary mounted on the tip of an inverted conical container, volume about 500 µL, i.e. a funnel-shaped device, to the upper end of which is attached a pressure applicator.

The capillary is lowered into a 9 mm internal diameter, round-bottomed well in an assay cartridge (as described for the previous Examples) containing 200 µL of an aqueous boronic acid conjugate solution.

The conjugate solution comprises 0.25 mM xylene-cyanole boronic acid conjugate (Example 18 of U.S. Pat. No. 5,631,364), 0.07% w/v Triton X-100, 9 mM zinc chloride, and 100 mM HEPES buffer, pH 8.15.

The blood sample is pumped into the well and mixed with the boronic acid conjugate solution by pumping the solution into and out of the conical container three times. The capillary is removed and the well contents are allowed to incubate for two minutes. This permits the detergent to lyse the blood cells, the zinc to precipitate the hemoglobin and the boronic acid conjugate to bind to glycated hemoglobin.

The membrane-tipped pipette is then lowered into the well and below ambient pressure is applied causing the liquid in the well to pass into the pipette and the hemoglobin to become trapped on the membrane. In this assay the membrane is a porous filter having a 1 µm pore size.

The pipette is removed from the well and placed in a second well of the same configuration containing 200 µL of an aqueous washing reagent (50 mM morpholine buffer, pH 9.5, containing 200 mM NaCl, 0.5% w/v Triton X-100, 0.1% w/v glycerol and 0.05% w/v $NaN_3$. Below ambient pressure is applied to the pipette drawing the washing reagent and unbound boronic acid conjugate into the pipette.

The pipette is then removed and lowered into a 9 mm internal diameter, flat bottomed, empty reading well in the cartridge for reflectometric measurement of the hemoglobin trapped on the pipette membrane. Total hemoglobin is measured using blue light at 460 nm and glycated hemoglobin using red light at 620 nm (e.g. using red and blue LREDs). The proportion of glycated hemoglobin relative to total hemoglobin (sometimes referred to as %Hb1Ac) is determined by the ratio of the measured reflectancies, calibrated against samples with known %Hb1Ac.

Figure 8:
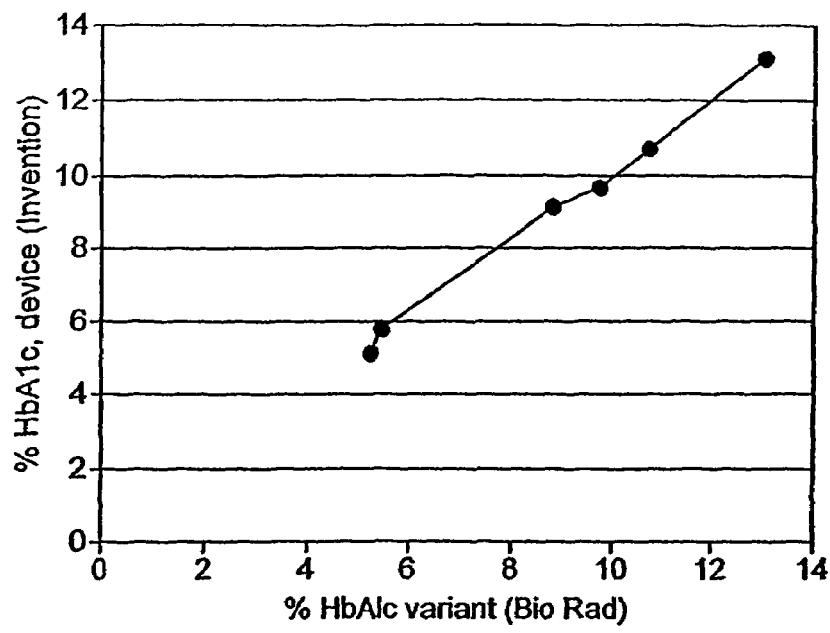
FIG. 8 shows the results of the assay of Example 3.

FIG. 8 of the accompanying drawings shows the results for the assay of this Example for 6 blood samples analysed for %Hb1Ac 24 hours earlier using HPLC (Variant, BioRad).

EXAMPLE 4

Liquid Collection Efficiency for Membrane-tipped Pipettes

The efficiency of liquid collection from different well configurations was tested for a planar nitrocellulose membrane-tipped pipette as described in Example 1 in comparison with a standard conical, open-tipped pipette. In each case 200 µL of liquid was to be withdrawn from a flat or round bottomed 9 mm internal diameter well in a soft or hard plastic base (LDPE and polystyrene respectively). The results are set out in Table 1 below.

TABLE 1

| | % Liquid collected | |
|---|---|---|
| Well | Open-tipped pipette | Membrane-tipped pipette |
| Soft, round | 98.9 | 99.8 |
| Hard, round | 99.5 | 99.7 |
| Hard, flat | 84.0 | 99.5 |

EXAMPLE 5

Assay for Coagulation Time for Blood

The pipette of FIG. 5 is used to collect an approximately 2 µL sample of blood. The cartridge is then reassembled and pressure is applied to the pipette to expel the blood sample into a cartridge well, the base of which is coated with a coagulation promoting agent (e.g. tissue factor). Below ambient pressure is then applied to draw the sample back into the pipette, past the chamber into the sinuous capillary. The sample is then shuttled back and forth in the sinuous capillary under the application of above ambient and sub-ambient pressures and, using the digital camera, the time between the blood sample contacting the coagulation promoting agent and effective cessation of blood sample movement is determined. This may typically be about 40 seconds.

EXAMPLE 6

Assay for Coagulation Time for Whole Blood or Plasma

An assay cartridge of the type shown in FIG. 11 is used. One of wells 59 to 62 contains dried tissue factor and calcium chloride or gluconate as well as a steel ball, e.g. 2 mm diameter (see FIG. 19a).

The apparatus into which the cartridge is to be placed is provided with a heating element to maintain the cartridge contents at about 37° C. and with a magnet to shuttle the steel ball along the base of the well in which is disposed.

In well 57 is disposed a removable capillary tipped pipette capable of taking up a preset volume of sample, e.g. 1 to 15 μL, preferably 10 μL, of whole blood, citrated venous blood, plasma or citrated plasma.

The sample is taken up by the capillary-tipped pipette which is then placed in the cartridge which is then placed in the assay apparatus. The sample is then transferred into the steel ball-containing well and mixed.

The cartridge is then shuttled relative to the magnet in a horizontal direction parallel with the tip of the ball containing well. (Either the cartridge as a whole or the magnet may be moved—however preferably the cartridge is moved with the magnet serving initially to keep the steel ball static.)

A digital camera is used to monitor the position of the steel ball. As the mixture begins to coagulate the ball ceases to be static relative to the magnet and this is detected by the camera so allowing the clotting time (from contact of sample with calcium salt solution) to be determined.

In an alternative, less preferred, embodiment, the magnet beneath the cartridge is omitted and the ball is placed in a well with a sloping base (e.g. as shown in FIG. 19b). Sharp movement of the cartridge in the direction of the lower end of the base, e.g. through mechanical shock or by activation of an electromagnet to the side of the well, causes the ball to move up the sloping base and, before clotting occurs, the ball returns to the lower end of the base under the action of gravity.

EXAMPLE 7

Assay for Coagulation Time for Whole Blood or Plasma

An assay cartridge as in Example 6 is used with a low density polymer ball (e.g. a polystyrene ball 3-5 mm in diameter) in place of the steel ball. This ball is preferably in a flat or concave-bottomed, circular cross section well (see FIG. 19c).

A sample is taken and mixed as in Example 6 and then placed in the ball-containing well where the ball will float on the sample surface. The ball is then repeatedly urged under the sample surface and allowed to float back up to the surface. As the sample coagulates the ball will return to the surface more slowly and then not at all.

The ball may be urged under the surface by pressure from the tip of the pipette or alternatively a magnetically movable ball may be used and a magnetic field may be switched on and off to draw the ball down and release it respectively. Such magnetically responsive balls may be prepared for example by depositing superparamagnetic crystals in the polymer ball (e.g. as in the magnetic beads sold by Dynal Biotech, Oslo, Norway).

EXAMPLE 8

Assay of Clotting Time for Plasma

An assay cartridge similar to that shown in FIG. 11 is used. As in Example 6, one of wells 59 to 62 contains a citrate buffer, another contains fibrinogen and coagulation factor V and a third a calcium salt solution. Well 57 contains a capillary-tipped pipette and well 58 contains a filter extension as shown in FIG. 18.

A sample is taken up in the capillary tipped pipette which is then placed in well 57 and the cartridge is placed in the assay apparatus and there warmed to 37° C. The sample is then transferred to the buffer-containing well and mixed. The whole or a preset proportion of the mixture is then transferred into the filter pipette extension and cell-free diluted plasma is pumped into the base of the well. A predetermined volume of cell-free plasma is then transferred into the fibrinogen containing well using a further capillary tipped pipette and this further pipette is also used to transfer a predetermined volume of the calcium salt solution to the fibrinogen/plasma containing well to initiate the clotting-reaction. The well is illuminated and a digital camera is used to record the turbidity of the mixture in the well. The time from calcium addition to increase of turbidity to a pre-defined value is taken as the clotting time.

EXAMPLE 9

Assay for Clotting in Whole Blood or Plasma

An assay cartridge similar to that shown in FIG. 11 and described in Example 8 is used. As in Example 8, one of wells 59 to 62 contains citrate buffer and another a calcium salt solution, however the ball-containing well is omitted and in place of coagulation factor V and fibrinogen the "reagent" well contains a dried thrombin-specific chromogenic substance (e.g. Nycotest Chrom (described in Janson et al. Thrombostasis and Haemostasis 62: 530 (poster 1677) (1989) and Jonker et al. Research in Clinic and Laboratory 20: 45-57 (1990)) or one of the chromogenic substances discussed in DE-A-3113350, DE-A-3413311, DE-A-3311287, U.S. Pat. No. 4,458,015 or U.S. Pat. No. 4,784,944).

The sample is taken and mixed analogously to the procedure in Example 7. The coagulation process results in thrombin formation and thus the release of a dye from the chromogenic substance (e.g. yellow para-nitroaniline from Nycotest Chrom).

The change in colour of the sample is followed using the digital camera and the clotting time is taken as the time from calcium addition to a predetermined colour change.

EXAMPLE 10

Assay for C-reactive Protein (CRP) in Whole Blood Using Enzyme Conjugate (ELISA)

Using the capillary-tipped pipette of the cartridge; 1 μL whole blood is added to a well (e.g. well 59) of a cartridge similar to that shown in FIG. 11 and containing 200 μL of a dilution and lysing liquid (30 mM borate buffer pH 8.0 containing 0.01% w/v sodium citrate, 0.02% w/v $NaN_3$ and dexoycholate). The wells of the cartridge have a rectangular cross section with inner dimensions 6.0 by 6.5 mm. The planar bottom of the well is angled 30 degrees to the length axis of the well.

The rectangular membrane-tipped pipette (which has outer dimensions 3.7 by 4.2 mm and is equipped with an anti CRP antibody-coated nitrocellulose membrane mounted 30 degrees to the length axis of the membrane tube) is lowered into the well and the lysed blood cell solution is absorbed through the membrane by applying below ambient pressure to the interior of the membrane-tipped pipette. When all liquid is absorbed, an above ambient pressure is applied to force the liquid a second time through the membrane and back into the well. Passing the CRP solution twice through the membrane increases further the capture efficiency of CRP.

Subsequently the membrane-tipped pipette is moved to a similar well (e.g. well 60) in the cartridge which contains a solution of alkaline phosphatase (ALP) conjugated to an anti CRP antibody (approximately 40 µg/ml ALP and 40 µg/ml antibody in 50 mM borate buffer pH 8.0 containing 0.02% w/v $NaN_3$ and 0.5% w/v BSA. The conjugate solution is absorbed through the membrane and pumped back into the well by applying a sequence of below and above ambient pressure inside the membrane-tipped pipette as described above for the antigen capture.

In the next step, the membrane-tipped pipette is moved to a further well (e.g. well 61) in the cartridge which contains 200 µL of washing solution (50 mM borate buffer pH 8.0 containing 0.01% w/v $NaN_3$, 0.5% w/v BSA and deoxycholate) which is absorbed and subsequently pumped back into the well. This washing step is repeated twice by moving the membrane-tipped pipette to two additional wells (not shown in FIG. 11 but equivalent to well 61) which also contain the washing solution. The total of three washing cycles ensures an efficient removal of unbound conjugate.

Finally the membrane-tipped pipette is moved into a still further well (e.g. well 62) in the cartridge which contains 300 µL of a solution of the alkaline phosphatase substrate para nitrophenyl phosphate (1.0 mg/ml pNPP in 1.0 M diethanolamine buffer pH 9.6 containing 0.5 mM $MgCl_2$ and 0.025% w/v $NaN_3$). The yellow enzyme product para-nitrophenol is developed by pumping the substrate solution in and out of the membrane-tipped pipette over a period of two minutes. The incubation is terminated by pumping all liquid back into the well and raising the membrane-tipped pipette out of the substrate solution. Using 300 µL of substrate solution the filling height is about 3 mm above the top of the angled part of the well, thus allowing the colour to be measured through parallel walls of the well.

With the membrane-tipped pipette raised, the absorbance is measured using a blue LED as a light source and a digital camera for measurement of transmitted light.

EXAMPLE 11

Assay for C-reactive Protein (CRP) in Whole Blood Using Light Scatter Measurement of Aggregated Latex Beads Using the capillary-tipped pipette of the cartridge, 2 µL whole blood is added to a well (e.g. well 62) of a cartridge similar to that shown in FIG. 11 and containing 120 nm Latex beads (0.2% w/v) suspended in 300 µL 50 mM borate buffer pH 8.0 containing 0.01% w/v sodium citrate, 0.02% w/v $NaN_3$ and deoxycholate. The beads are coated by simple adsorption with anti CRP antibodies. The well has a rectangular cross section and is at the end of the cartridge to facilitate the measurement of light scatter. Light is directed onto one side wall of the well. After an initial phase of cell lysis which takes about 10 seconds, the increase of light scatter is measured at an angle of 90 degrees to the incident light. The increase of light scatter due to the CRP-mediated aggregation of the Latex beads is measured by the digital camera at a wavelength of 425 nm.

EXAMPLE 12

Assay for Albumin in Urine Using Magnetic Beads Coloured Latex Beads and Relectometry Using the capillary-tipped pipette of the cartridge, 2 µL urine is added to a well (e.g. well 62) of a cartridge similar to that shown in FIG. 11 and containing 1000 nm magnetic polymer beads (0.2% w/v) and 1000 nm blue Latex beads (0.2 L w/v) in 200 µL 30 mM sodium phosphate buffer pH 5.7 containing 0.5% w/v BSA and 0.05% w/v $NaN_3$. The magnetic beads (e.g. of the type available from Dynal Biotech, Oslo, Norway) are coated with an antibody reacting with an epitope on the albumin molecule different from the epitope recognized by the antibody coated onto the Latex beads.

After incubation for 60 sec, a Neodymium magnet (10× 7×2 mm) is moved from its resting position (20 mm from the nearest wall of the well) towards the well to bring the magnet in direct contact with the side wall of the well. The magnet makes contact with the wall opposite to the angled one and covers the liquid filled part of the well (200 µL). The well and the positioning of the magnet are shown schematically in FIG. 20. In the resting position the magnetic field working on the magnetic beads is too weak to move the beads. When in contact with the well, the distance from the magnet to the nearest and remotest inner wall of the well is 0.8 mm and 6.3 mm respectively. At this distance the beads are quantitatively collected on the wall after 30 sec. In the presence of analyte, blue Latex is linked to magnetic particles and the reacted fraction of the Latex beads will be collected on the wall while unreacted Latex particles will remain suspended.

With the magnet in contact position, the capillary-tipped pipette is used to suck up the liquid containing the unreacted Latex particles. The magnet is then moved away from the well to its resting position.

The capillary-tipped pipette tube is then moved into an empty well (e.g. well 61) and the liquid is delivered to this well by applying above ambient pressure to the interior of the pipette.

The capillary-tipped pipette is then moved to a further well (e.g. well 60) which contains 500 µL of washing solution (PBS, pH 7.4) and 200 µL is taken up. The capillary-tipped pipette is then moved back to the well containing the magnetic beads and the beads are suspended by pumping the washing solution in and out of the well five times. The magnet is moved into the contact position and the magnetic beads are allowed to be collected on the wall of the well. After 30 sec the washing solution is taken back into the capillary-tipped pipette. The magnet is subsequently moved back to its resting position.

The capillary-tipped pipette is in-the next step moved to the well containing the first supernatant (well 61) and pumped into this well.

The capillary-tipped pipette is subsequently moved to the well containing the washing solution (well 60) and 200 µL are taken up.

The capillary-tipped pipette is moved to the well containing the magnetic beads (well 62) and the beads are resuspended by pumping the washing solution in and out 5 times.

A membrane-tipped pipette equipped with a 0.45 µm microporous membrane is moved to the well containing the suspended magnetic beads (well 62) and the beads are collected onto the membrane by suction.

The membrane-tipped pipette is raised out of well 62 and blue Latex particles and the yellow-brown magnetic beads are quantified by reflectometry using a red LED for the blue Latex beads and a blue LED for the magnetic beads. The amount of absorbed red light/amount of absorbed blue light is a measure of the fraction of blue Latex in the mixture and hence a measure of the amount of albumin present in the sample.

The same cartridge may also be used for determination of creatinine content of urine and hence the albumin:creatinine ratio in the urine sample. Albumin in urine provides an indicator of kidney function and the albumin:creatinine ratio may be used to correct for diuresis. Albumin:creatinine measurement is described for example in U.S. Pat. No. 5,385,847.

In this embodiment a fraction of the urine sample is mixed with a dilution reagent and an enzyme or enzyme mixture which reacts with creatinine to generate a coloured analyte which is detected using a digital camera by measurement of light transmission through a well containing urine, enzymes and dilution reagent.

The invention claimed is:

1. An assay cartridge comprising at least two wells and a membrane-tipped pipette positionable in at least two of said wells, said membrane-tipped pipette having a proximal end and a distal end, said distal end being closed by a liquid permeable membrane, wherein said cartridge further comprises a capillary-tipped pipette.

2. An assay cartridge as claimed in claim 1 wherein said membrane-tipped pipette is closed by a sloping liquid permeable membrane.

3. An assay cartridge as claimed in claim 2 wherein said sloping membrane lies in a plane at an angle of 20 to 40° to the axis of said membrane-tipped pipette to which it is attached.

4. An assay cartridge as claimed in claim 1 wherein said a membrane-tipped pipette has a membrane-tipped end is of rectangular cross section.

5. An assay cartridge as claimed in claim 1 wherein said cartridge comprises detachable base and cap members, said wells being disposed in said base member and said cap member being arranged to carry said membrane-tipped pipette positionable in at least two of said wells.

6. An assay cartridge as claimed in claim 5 wherein said cap member comprises means to receives said capillary-tipped pipette.

7. An assay cartridge as claimed in claim 5 wherein at least one of said wells is sealed at its upper end by a frangible seal and wherein said cap member is provided with a cutter arranged to pierce said seal.

8. An assay cartridge as claimed in claim 5 wherein said base member comprises an absorbent wiper arranged to wipe the outside of said capillary-tipped pipette inserted therein.

9. An assay cartridge as claimed in claim 1 wherein said membrane-tipped pipette the proximal end whereof is closed by a piercable self-sealing membrane.

10. An assay cartridge as claimed in claim 1 wherein the wells in said cartridge are arranged in a linear array.

11. An assay cartridge as claimed in claim 1 wherein at least one of said wells contains an assay reagent.

12. An assay cartridge as claimed in claim 1 wherein said capillary tip is provided with a detachable sleeve.

13. An assay cartridge as claimed in claim 1 wherein at least one said well has two parallel planar side walls joined by a base wall comprising at least one planar face a normal to the surface whereof is coplanar to and non-perpendicular to normals to the parallel planar surfaces of said side walls.

14. An assay device comprising a) a cartridge holder capable of receiving an assay cartridge comprising at least two wells and a membrane-tipped pipette positionable in at least two of said wells, said membrane-tipped pipette having a proximal end and a distal end, said distal end being closed by a liquid permeable membrane; b) drive means operable to position said membrane-tipped pipette of said cartridge in selected wells of said cartridge; c) a gas pressure applicator couplable to said membrane-tipped pipette of said cartridge whereby to cause liquid flow therethrough; and d) a radiation detector operable to detect radiation from said well of said cartridge or from said membrane-tipped pipette thereof 15. A device as claimed in claim 14 wherein said radiation detector comprises a digital camera.

16. A device as claimed in claim 14 further comprising a light source arranged to illuminate said cartridge.

17. A device as claimed in claim 14 further comprising a magnet.

18. A device as claimed in claim 14 further comprising a heater arranged to heat said cartridge.

19. A device as claimed in claim 14 further comprising a controller arranged to control assay performance by said apparatus.

20. A device as claimed in claim 14 wherein said gas pressure applicator comprises a piston disposed within a cylindrical housing and a drive motor arranged to drive said piston.

* * * * *

UNITED STATES PATENT AND TRADEMARK OFFICE
CERTIFICATE OF CORRECTION

PATENT NO. : 7,632,462 B2
APPLICATION NO. : 10/476185
DATED : December 15, 2009
INVENTOR(S) : Holtlund et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1547 days.

Signed and Sealed this

Twenty-first Day of December, 2010

David J. Kappos
*Director of the United States Patent and Trademark Office*